(12) United States Patent
Spiegelberg et al.

(10) Patent No.: US 6,884,264 B2
(45) Date of Patent: Apr. 26, 2005

(54) SYSTEM AND METHODS FOR REDUCING INTERFACIAL POROSITY IN CEMENTS

(75) Inventors: Stephen H. Spiegelberg, Winchester, MA (US); Jeffrey W. Ruberti, Lexington, MA (US); Gavin G. C. Braithwaite, Cambridge, MA (US)

(73) Assignee: Cambridge Polymer Group, Inc., Boston, MA (US)

( * ) Notice: Subject to any disclaimer, the term of this patent is extended or adjusted under 35 U.S.C. 154(b) by 0 days.

(21) Appl. No.: 10/102,446

(22) Filed: Mar. 19, 2002

(65) Prior Publication Data

US 2002/0183851 A1 Dec. 5, 2002

Related U.S. Application Data

(60) Provisional application No. 60/276,592, filed on Mar. 19, 2001.

(51) Int. Cl.$^7$ .................................................. A61F 2/32
(52) U.S. Cl. ........................ 623/22.12; 606/92; 606/99
(58) Field of Search ...................... 623/22.12; 606/92, 606/99

(56) References Cited

U.S. PATENT DOCUMENTS

| | | | | |
|---|---|---|---|---|
| 4,837,279 A | | 6/1989 | Arroyo | 525/193 |
| 4,977,115 A | | 12/1990 | Klein et al. | 501/107 |
| 5,037,442 A | * | 8/1991 | Wintermantel et al. | 623/23.16 |
| 5,045,054 A | | 9/1991 | Hood et al. | 604/22 |
| 5,284,484 A | * | 2/1994 | Hood et al. | 606/99 |
| 5,382,251 A | * | 1/1995 | Hood et al. | 606/99 |
| 5,456,686 A | * | 10/1995 | Klapper et al. | 606/99 |
| 5,480,450 A | | 1/1996 | James et al. | 623/23 |
| 5,536,266 A | * | 7/1996 | Young et al. | 606/27 |
| 5,681,872 A | * | 10/1997 | Erbe | 523/114 |
| 5,885,495 A | | 3/1999 | Ibar | 264/69 |
| 5,913,899 A | | 6/1999 | Barrett et al. | 623/18 |
| 6,005,163 A | | 12/1999 | Tepic | 623/16 |
| 6,136,035 A | | 10/2000 | Lob et al. | 623/23 |
| 6,139,584 A | | 10/2000 | Ochoa et al. | 623/23.46 |
| 6,165,177 A | * | 12/2000 | Wilson et al. | 606/100 |
| 6,203,747 B1 | | 3/2001 | Grunitz | 264/443 |
| 6,210,030 B1 | | 4/2001 | Ibar | 366/78 |

FOREIGN PATENT DOCUMENTS

| | | |
|---|---|---|
| GB | 2277448 A | 11/1994 |
| WO | WO 90 04953 | 5/1990 |

OTHER PUBLICATIONS

Bundy, K. J, & Penn R. W., "The effect of surface preparation on metal/bone cement interfacial strength," *J. of Biomedical Research*, vol. 21, 773–805 (1987).

(Continued)

*Primary Examiner*—Corrine McDermott
*Assistant Examiner*—Thomas J Sweet
(74) *Attorney, Agent, or Firm*—Bowditch & Dewey, LLP

(57) ABSTRACT

The present invention provides a system and a method for reducing pores, or air pockets, that form at the interface between the material used to attach or adhere the surface of a component, such as a prosthesis, to a site.

A preferred embodiment of the invention includes an actuator that controls a coupler which transmits energy to a prosthesis being inserted into a material to reduce porosity at an interface between the prosthesis and the material.

The system of the present invention can include an oscillating hand-held device that vibrates the stem component of an orthopedic prosthesis at a particular frequency and amplitude. The device is typically held by the hand of the surgeon, who guides the vibrating prosthesis into the cement-filled medullary cavity.

82 Claims, 32 Drawing Sheets

OTHER PUBLICATIONS

Lewis, G., "Effect of Mixing Method and Storage Temperature of Cement Constituents on the Fatigue and Porosity of Acrylic Bone Cement," University of Memphis, Memphis, Tennessee, Mar. 1998.

Verdonschot N., & Huiskes, R., "The Effects of Cement–Stem Debonding in THA on the Long–Term Failure Probability of Cement," *J. Biomechanics*, vol. 30, No. 8, pp. 795–802, 1997.

Lewis, G., "Properties of Acrylic Bone Cement: State of the Art Review," The University of Memphis, Memphis, Tennessee, Feb. 1997.

Schmalzried, T. P., et al., "The Significance of Stem–Cement Loosening of Grit–Blasted Femoral Components," *Orthopedics*, vol. 23, No. 11, Nov. 2000.

Gilbert, J. L., et al., "A theoretical and experimental analysis of polymerication shrinkage of bone cement: A potential major source of porosity," accepted Feb. 16, 2000.

James, S.P., et al., "A fractographic investigation of PMMA bone cement focusing on the relationship between porosity reduction and increased fatigue life," *Journal of Biomedical Materials Research*, vol. 26, 651–662, (1992).

Harris, J. & Wilkinson, W.L., "Non–newtonian Fluid," McGraw–Hill Encyclopedia of Physics, Second Ed., McGraw Hill, New York, p 856–858 (1993).

Howmedica Products: Partnership™ System, Merdian ™ PA Femoral Component, [retrieved on Mar. 17, 2002]. Retrieved from the Internet <URL:http://www.ostenoics.com/howmedica/products/frames/prod2f.htm>.

Howmedica Products: Exeter Total Hip System, Unique Stem Design, [retrieved on Mar. 17, 2002]. Retrieved from the Internet <URL:http://www.ostenoics.com/howmedica/products/frames/prod2p2b.htm>.

Howmedica Products: Exeter Total Hip System, Increased Compression at Stem/Cement Interface, Cement–An Integral Solution, [retrieved on Mar. 17, 2002]. Retrieved from the Internet <URI:http://www.ostenoics.com/howmedica/products/frames/prod2p2d.htm>.

Material Safety Data Sheet, [retrieved on Mar. 17, 2002]. Retrieved from the Internet <URL:http://www.ostenoics.com/hcp/pages/msds2000.html>.

Stryker® Howmedica Osteonics, Facts for Operating Room Nurses, History, [retrieved on Mar. 17, 2002]. Retrieved from the Internet <URL:http://www.osteonics.com/hcp/or_nurse/pages/history.html.>.

Stryker® Howmedica Osteonics, The Formula for Success, 40 Years of Clinical Success, [retrieved on Mar. 14, 2002]. Retrieved from the Internet <URL:http://www.osteonics.com/simplex_us/pages/intro.html.>.

Class II Special Controls Guidance Document: Polymethylmethacrylate (PMMA) Bone Cement 510(k)s; Final Guidance for Industry, Center for Devices and Radiological Health, Aug. 2, 2001.

Verdonschot, N., Tanck, E., Huiskes, R., "Effects of prosthesis surface roughness on the failure process of cemented hip implants after stem–cement debonding," J. Biomed. Mater. Res., 42, 554–559 (1998).

Beaumont, P.W.R., "The strength of acrylic bone cements and acrylic cement–stainless steel interfaces," *J. Mater. Sci.*, 12:1845–1852 (1977).

Bishop, N.E., et al., "Porosity Reduction in Bone Cement at the Cement–Stem Interface," *J. Bone and Joint Surg.*, 78–B(3):349–356 (1996).

Crowninshield, R.D., et al., "Cement strain measurement surrounding loose and well–fixed femoral component stems," *J. Biomed. Mater. Res.*, 17:819–828 (1983).

Davies, J.P., et al., Strength of Cement–Metal Interfaces in Fatigue: Comparison of Smooth, Porous and Precoated Specimens; *Clin. Mater.*, 12:121–126 (1993).

Davies, J.P., et al., "Effect of Interfacial Porosity on the Torsional Strength of the Cement–Metal Interface," *Proc. 41st Ann. Meeting ORS.*, 713 (1995).

Gruen, T.A., et al., "Modes of Failure of Cemented Stem–type Femoral Components," *Clin. Orthop. Relat. Res.* 141:17–27 (1979).

Hampton, S.J., et al., "Stresses Following Stem Cement Bond Failure in Femoral Total Hip Implants," *Trans. 27th Ann. Orthop. Res. Soc.*, 144 (1981).

Harrigan, T.P., et al., "A Three–Dimensional Non–Linear Finite Element Study of the Effect of Cement–Prosthesis Debonding in Cemented Femoral Total Hip Components," *J. Biomech.*, 24(11):1047–1058 (1991).

Harrigan, T.P., et al., "A Finite Element Study of the Initiation of Failure of Fixation in Cemented Femoral Total Hip Components," *J. Ortho. Res.*, 10:134–144 (1992).

Harris, W.H., et al., "Modern Use of Modern Cement for Total Hip Replacement," *Orthop. Clin. North Am.*, 19(3):581–589 (1988).

Harris, W.H.; et al., An overview of rough surfaced cemented femoral implants, Total Hip Replacements: the dawn of a New Era, Cambridge, MA (1998).

Huiskes, R. "Characterization and Preperties of Bone–Implant System," *Acta Orthop. Scand. Suppl.*, 185:19–69 (1980).

Jaffe, W.L., et al., "Normalized and Proportionalized Cemented Femoral Stem Designs" *J. Arthroplasty*, 10 Supplement (1995).

Jasty, M., et al., "Porosity of Various Preparations of Acrylic Bone Cements," *Clin. Orthop.*, 259:122–129 (1990).

Jasty, M., et al., "The Initiation of Failure in Cemented Femoral Components of Hip Arthroplasties," *J. Bone and Joint Surg.* 73–B(4):551–558 (1991).

James, S.P., et al., "Extensive porosity at the cement–femoral prosthesis interface: A preliminary study," *J. Biomed. Mater. Res.*, 27:71–78 (1993).

James, S., et al., "Porosity Reduction at the Femoral Prosthesis/Cement Interface," *17th Ann Meet. Soc. Biomaterials*, 50 (1991).

Maloney, W.J., et al.; Biomechanical and Histologic Investigation of Cemented Total Hip Arthroplasties: A Study of Autopsy–Retreived Femurs After In Vivo Cycling; Clin. Orthop., 249:129 (1989).

Mann, K.A., et al., "Cement Stresses in a Femoral Hip Component with Coulomb Friction at the stem–Cement Interface," *Trans. 37th Ann. Orthop. Res. Soc.*, 16, 107 (1991).

Raab, S., et al., "The quasistatic and fatigue performance of the implant/bone–cement interface," *J. Biomed. Mater. Res.*, 15:159–182 (1981).

Scholten, R., et al., "Analysis of stress distrubition in natural and artificial hip joints using the finite–element method," *South African Mech. Eng.*, 28:220–225 (1978).

Schmalzried, T.P., et al., "Autopsy Studies of the Bone–Cement Interface in Well–fixed Cemented Total Hip Arthroplasties" *J. Arthroplasty*, 8(2):179–188 (1993).

Spiegelberg, S.H., et al., "Characterization of the Curing Process of Bone Cement with Multi–harmonic Shear Rheometry," *24th Ann. Meeting of Soc. for Biomaterials* (1998).

Wester, W., et al., "Twenty year cemented femoral revisions, Total Hip Replacement: The Dawn of a New Era", Cambridge, MA (1998).

Welsh, P., et al., "Surgical Implants: The Role of Surface Porosity in Fixation to Bone and Acrylic," *J. Bone and Joint Surg.*, 53A(5):963–977 (1971).

* cited by examiner

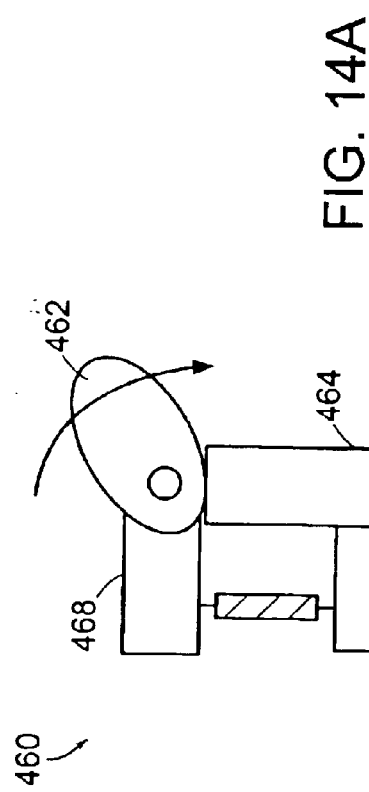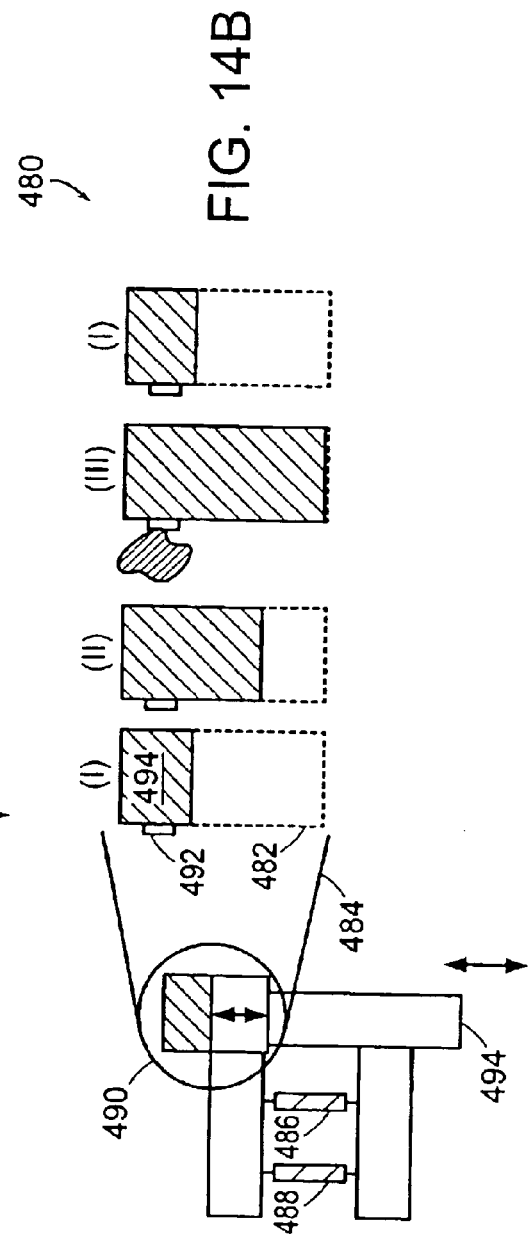

SYSTEM AND METHODS FOR REDUCING INTERFACIAL POROSITY IN CEMENTS

CROSS REFERENCES TO RELATED APPLICATIONS

The present application is related to co-pending PCT Patent Applications being filed on even date, having Attorney Docket No.: 301788.3001-101 entitled System and Methods For Reducing Interfacial Porosity in Cements by Stephen H. Spiegelberg, Jeffrey W. Ruberti and Gavin J. C. Braithwaite and claims priority to U.S. Provisional Application No. 60/276,592 filed on Mar. 19, 2001.

The entire contents of the above applications are incorporated herein by reference in entirety.

BACKGROUND OF THE INVENTION

There is an increase each year in the number of hip and knee total joint replacement surgeries, respectively total hip arthroplasties (THA) and total knee arthroplasties (TKA). Recently the number of surgeries exceeded 600,000 operations a year in the United States.

The cost of an initial total hip replacement remains high. Revision surgeries to replace a failed hip prosthesis are typically more difficult and consequently more expensive. The annual cost for a 3% revision rate can be estimated to reach approximately $1 billion in the U.S. There is a strong need to minimize any conditions that lead to failure of the initial surgery.

In failed total hip arthroplasties with cemented stems, it is estimated that 20% of revision surgeries result from loss of fixation at the interface between the bone cement and the metallic femoral stem component.

There is clear indication that indicates that excessive voids caused by bubbles at the interface of the bone cement and the stem component ("interfacial porosity") leads to failure of the joint between the stem component and the bone cement. This interfacial porosity reduces the area over which loads are transferred from the implant to the cement mantle, resulting in local stresses that exceed the yield strength of the interface. It is known that the degree of interfacial porosity is primarily controlled by the rheology of the curing cement and the interaction of the curing cement with the stem component during insertion.

In hip and knee total arthroplasties, surgeons often use bone cement to fix the femoral stem component or tibial component of the prosthesis in the respective bone. The bone cement is often in the form of a two-part polymethyl methacrylate grout. The surgeon mixes pre-polymerized polymethyl methacrylate (PMMA) beads with methyl methacrylate monomer in the presence of chemicals that initiate a free radical polymerization reaction. When the cement is partially polymerized, or "cured", so that the liquid cement is viscous enough to be retained in a reamed cavity in the tibia or femur it is injected under pressure into the cavity. After polymerization has proceeded for an additional determined period, the surgeon inserts the stem component of the prosthetic joint into the partially cured cement. The cement then fully cures, fixing the stem component in place.

Clinical studies of failed hip arthroplasties have shown that a large number of failures occur at the cement-stem interface. The cyclical loading pattern imposed on the interface between the cement and metallic stem makes them susceptible to fatigue crack growth. Failure analysis on bone cement specimens subjected to fatigue testing shows that crack formation often forms at pores, or gas pockets in the cement. Centrifugation and vacuum mixing are now commonly used to reduce pores in the bulk of the cement, but these procedures do not reduce the interfacial porosity to levels below or equal to the bulk porosity. An intact cement-stem interface will assure an even distribution of the applied load, and will consequently decrease stress concentration and reduce the likelihood of cement fracture.

Porosity at the interface between the cement and the stem component of the prosthesis can be a major cause of the failure of cemented prostheses. A study of the cement mantles from retrieved hip prostheses showed that the porosity at the interface between the cement and the stem component of the prosthesis was much higher than the porosity in the bulk cement. Controlled experiments with differing stem materials showed that the interfacial porosity of the cement did not depend on which metal was used to form the stem component of the prosthesis, but may be more related to the rheology, or flow behavior, of the bone cement.

A cement with a lower viscosity will fully contact the surface of the prosthesis and fill the areas left by displaced air. However, interfacial porosity can be more concentrated at the distal and proximal portions of the prosthesis, which is where failure usually occurs.

Others have examined cement rheology by evaluating stem components that were inserted into the cement at a stage when the cement was more fully polymerized. Thus, the viscosity of the cement was higher and the cement had more elastic behavior and tended to form more interfacial pores. Conversely, it was found that model stem components that were inserted into cement at a lower viscosity stage had a lower number of interfacial pores. The results of this study indicate the benefits of injecting the cement into the bone cavity, and later inserting the orthopedic implant into the cement-filled cavity, when the cement still has a lower viscosity.

However, hip and knee surgeries are performed with the patient in a prone position. Consequently, the cement cannot be injected into the bone cavity when the viscosity is low enough to prevent interfacial pore formation. The cement will flow out of the cavity into the wound, causing contamination and possible necrosis. Conversely, it is also critical that the cement be sufficiently viscous so that there is little movement of the stem component of the prosthesis after placement before the cement is fully cured. For this reason, surgeons routinely wait for about three quarters of the cure time before performing the insertion of the stem.

The desirability for low viscosity of the bone cement to minimize interfacial porosity and the likelihood of failure, competes with the need for sufficiently high viscosity to prevent movement of the stem component of the prosthesis after placement. A continuing need exists for improvements in systems and methods for implanting prosthesis to reduce failure rates in orthopedic implant procedures.

SUMMARY OF THE INVENTION

The present invention provides a system and a method for reducing pores, or air pockets, that form at the interface between the material used to attach or adhere the surface of a component, such as a prosthesis, to a site. The reduction of these interfacial pores reduces the likelihood of fracture of the material such as a cement mantle, which loosens the component, and ultimately may lead to failure of the structure and the need for replacement.

In a preferred embodiment of the invention the system and method of the present invention takes advantage of the shear-thinning properties of the partially-polymerized bone cement by vibrating the stem component as it is inserted into the bone cement, thereby reducing the viscosity locally at the cement-component interface. In another preferred embodiment of the invention the viscosity of the bone cement can be reduced by heating (or cooling) the stem component during insertion. In other preferred embodiments, the wetting of the stem component by the partially cured bone cement is enhanced by microchannels on the surface of the stem component or by other rough surface structures that increase surface area without increasing porosity.

A preferred embodiment of the invention includes an actuator that controls a coupler which transmits energy to a prosthesis being inserted into a material to reduce porosity at an interface between the prosthesis and the material.

The system of the present invention can include an oscillating hand-held device that vibrates the stem component of an orthopedic prosthesis at a particular frequency and amplitude. The device is typically held by the hand of the surgeon, who guides the vibrating prosthesis into the cement-filled medullary cavity.

The change in position of the stem component with time, called herein the "insertion profile", can be varied using the system and method of the present invention by varying four parameters: oscillation frequency, oscillation amplitude, insertion velocity and stem component temperature. The particular optimum ranges of these parameters are different depending on the physical characteristics of each individual bone cement. There can be several optimum combinations of these parameters for each bone cement.

The vibrational spectrum can be expressed in terms of the frequency of a fundamental using Fourier analysis. One or more higher harmonics may also be used, for example, in addition to the fundamental frequency. Suitable waveforms thus include a square wave, ramps and/or sine and cosine functions, for example. Suitable frequencies are greater than 0.1 rad/sec. Preferred frequencies are about 1 rad/sec to about 1000 rad/sec. In some preferred embodiments, frequencies are about 1 rad/sec to about 500 rad/sec.

Oscillation amplitudes can be expressed in terms of the diameter of the largest pre-polymerized bead in the dry bone cement that is being used. Suitable oscillation amplitudes are about 0.1 to about 50 times the diameter of the largest pre-polymerized bead. Preferred oscillation amplitudes are about 0.1 to about 5 times the diameter of the largest pre-polymerized bead. In some preferred embodiments, oscillation amplitudes are about 0.1 to about 10 times the diameter of the largest pre-polymerized bead. For bone cements in which diameter of the largest pre-polymerized bead in the dry bone cement is about 50 $\mu$m, for example, the oscillation amplitudes in preferred embodiments are about 5 $\mu$m to about 500 $\mu$m.

Suitable insertion velocities in preferred embodiment range from about 0.1 cm/sec to about 10 cm/sec. Preferred insertion velocities are about 0.25 cm/sec to about 5 cm/sec. In some preferred embodiments, insertion velocities are about 0.25 cm/sec to about 1 cm/sec. The insertion may be continuous, or alternatively, may include one or more pauses and thus be intermittent. In some preferred embodiments, the velocity is constant, with a preferred rate of about 0.1 to about 5 cm/sec, more preferably a rate of about 0.25 to about 3 cm/sec, most preferably about 0.5 to about 2 cm/sec. The insertion profile can also include one or more periods of acceleration, i.e., the plot of velocity vs. time can be described by an exponential or power law function. An insertion profile with acceleration can also include one or more pauses during the insertion. A preferred embodiment of the invention can include an insertion device to provide aligned insertion at a controlled rate.

The foregoing and other features and advantages of the system and method for reducing interfacial porosity in cements will be apparent from the following more particular description of preferred embodiments of the system and method as illustrated in the accompanying drawings in which like reference characters refer to the same parts throughout the different views.

BRIEF DESCRIPTION OF THE DRAWINGS

FIGS. 3A–3C are schematic diagrams illustrating the location of pores at the interface between a cement mantle and an orthopedic component, shown here as a femoral stem wherein FIGS. 3B and 3C are enlarged views of an interface section of FIG. 3A;

FIGS. 4A and 4B are scanning electron micrographs illustrating pores generated between a surface of an inserted stem and a cement mantle wherein FIG. 4A is a view that illustrates the pores when the stem is inserted early during the cure process (low viscosity) and FIG. 4B is a similar view but temporally after FIG. 4A illustrating the pores resulting late into the cure process (high viscosity), in accordance with a preferred embodiment of the present invention;

FIGS. 11A and 11B are schematic diagrams of two preferred embodiment systems including a vibration system wherein FIG. 11A is a piezo electric based system and FIG. 11B is an electromagnetic based system in accordance with the present invention;

FIG. 14A and FIG. 14B are alternate embodiments of drive mechanisms based on rotary motion and reciprocating drive, respectively, in accordance with a preferred embodiment of the present invention;

DETAILED DESCRIPTION OF THE INVENTION

Figure 1:
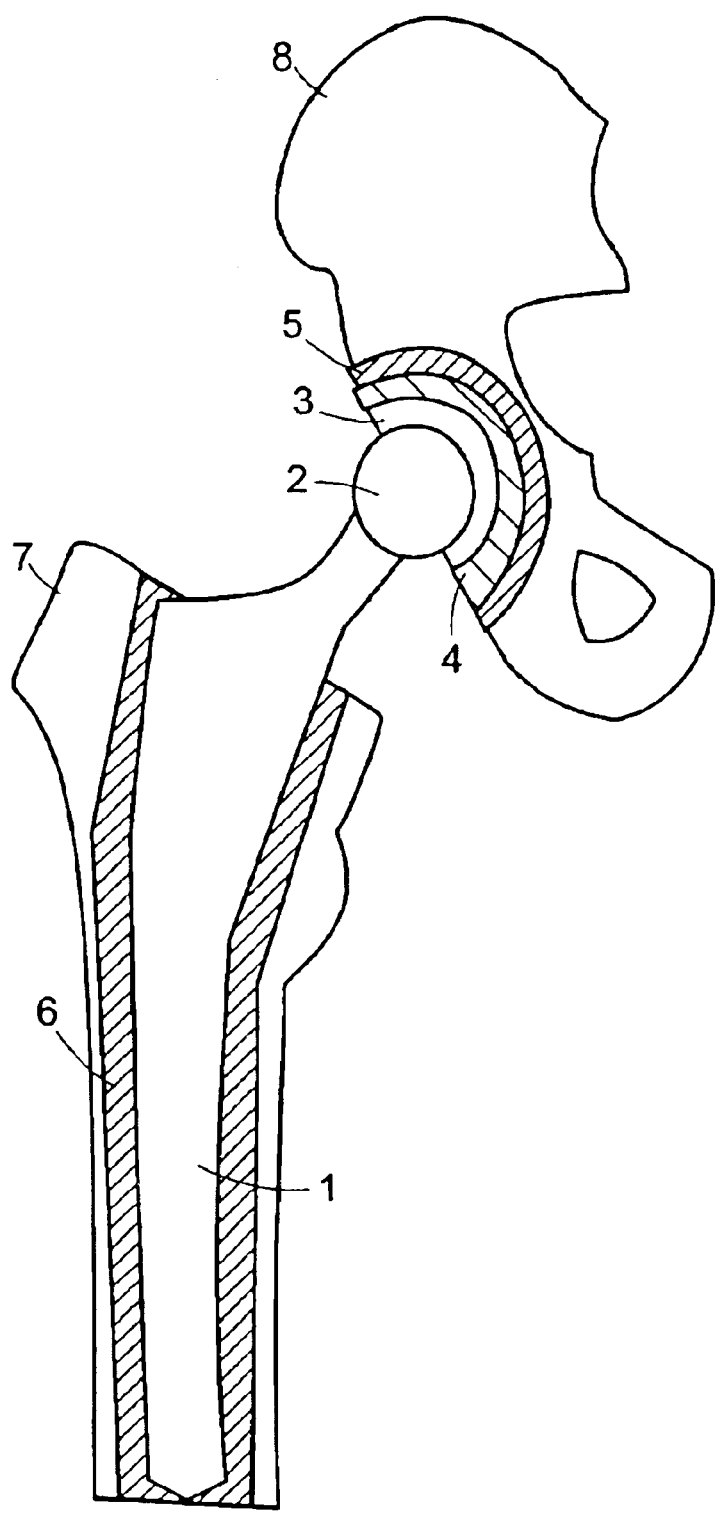
FIG. 1 is a diagrammatic view of a total hip prosthesis in accordance with a preferred embodiment of the present invention.

The present invention is directed at reducing interfacial pores that form at a surface of a component such as a prosthesis. As used herein "prosthesis" or "prosthetic" refer to a fabricated substitute for a damaged or missing part of the body or a portion thereof. As used herein "orthopedic implant" refers to a prosthesis, or portion thereof, suitable for implantation in the skeletal system, its articulations and associated structures. FIG. 1 is a diagrammatic view of a total hip prosthesis in accordance with a preferred embodiment of the present invention. Articulating movement of the femoral ball 2 in interfaces with the acetabular bearing surface 3 causes wear particles to be generated which are released into the space within the joint. This initiates the wear of the joint and causes the loosening of the joint necessitating a corrective operation. The prosthetic stem 1 is surrounded by bone cement mantle 6 in the femur 7. The femoral ball 2 in the acetabulum insert interfaces with the acetabular bearing surface 3. A metallic acetabulum shell 4 interfaces with the bearing surface and may be surrounded by bone cement mantle 5 in the hip 8.

Figure 2A:
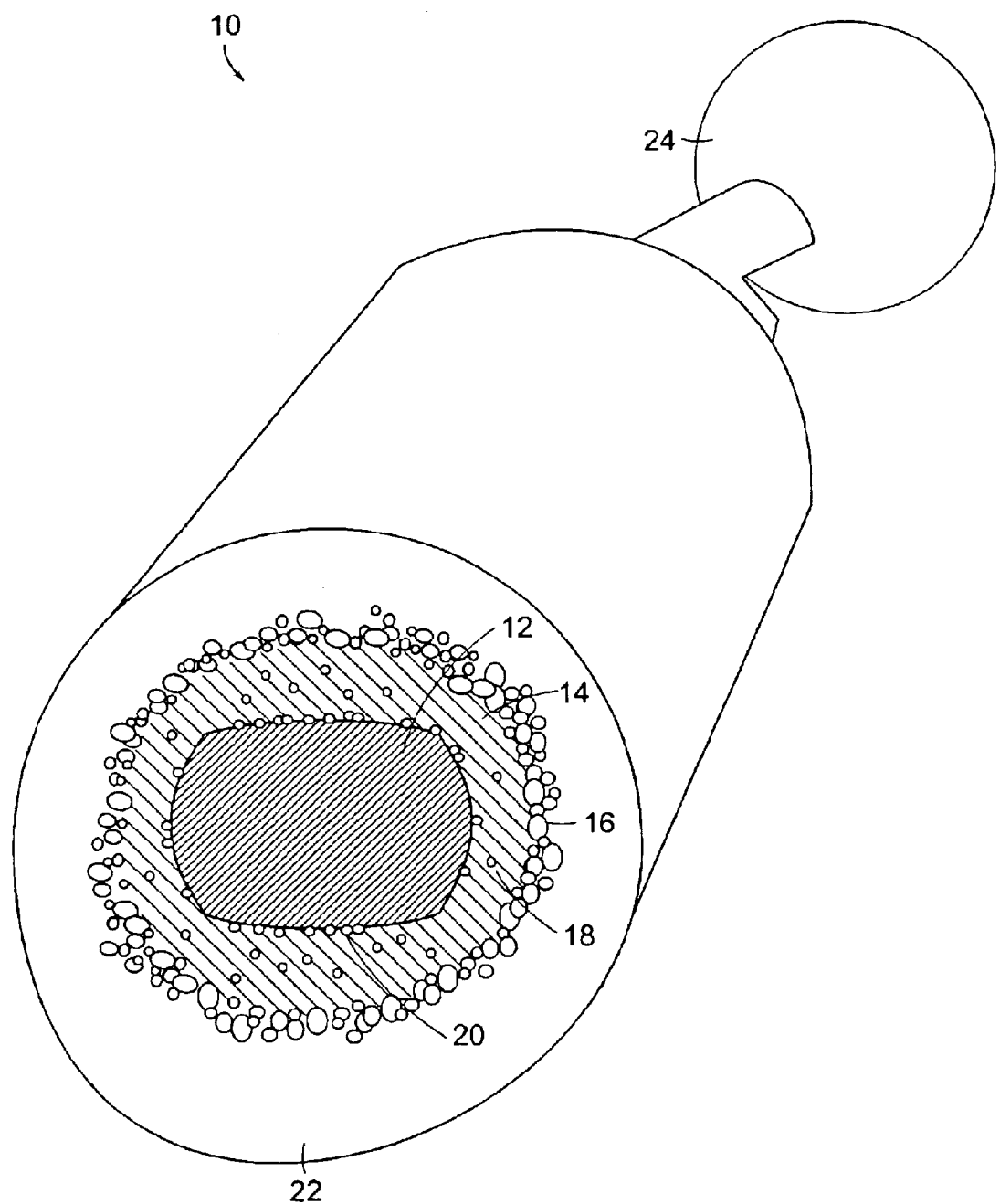
FIG. 2A is a schematic cross-sectional view of a hip implant using systems and methods in accordance with a preferred embodiment of the present invention.

The problem of interfacial porosity is illustrated by FIGS. 2A. FIG. 2A is a schematic diagram of the proximal portion of a femur 10 after a hip arthroplasty showing in cross section the spatial relationship of the femoral stem component 12 of a joint prosthesis (with femoral ball 24) to the surrounding bone cement mantle 14 and the adjacent cancellous bone 16 and compact bone 22. Voids and pores are found in the bulk of the cement 18 and at the interface between the stem component and the bone cement 20.

Figure 2B:
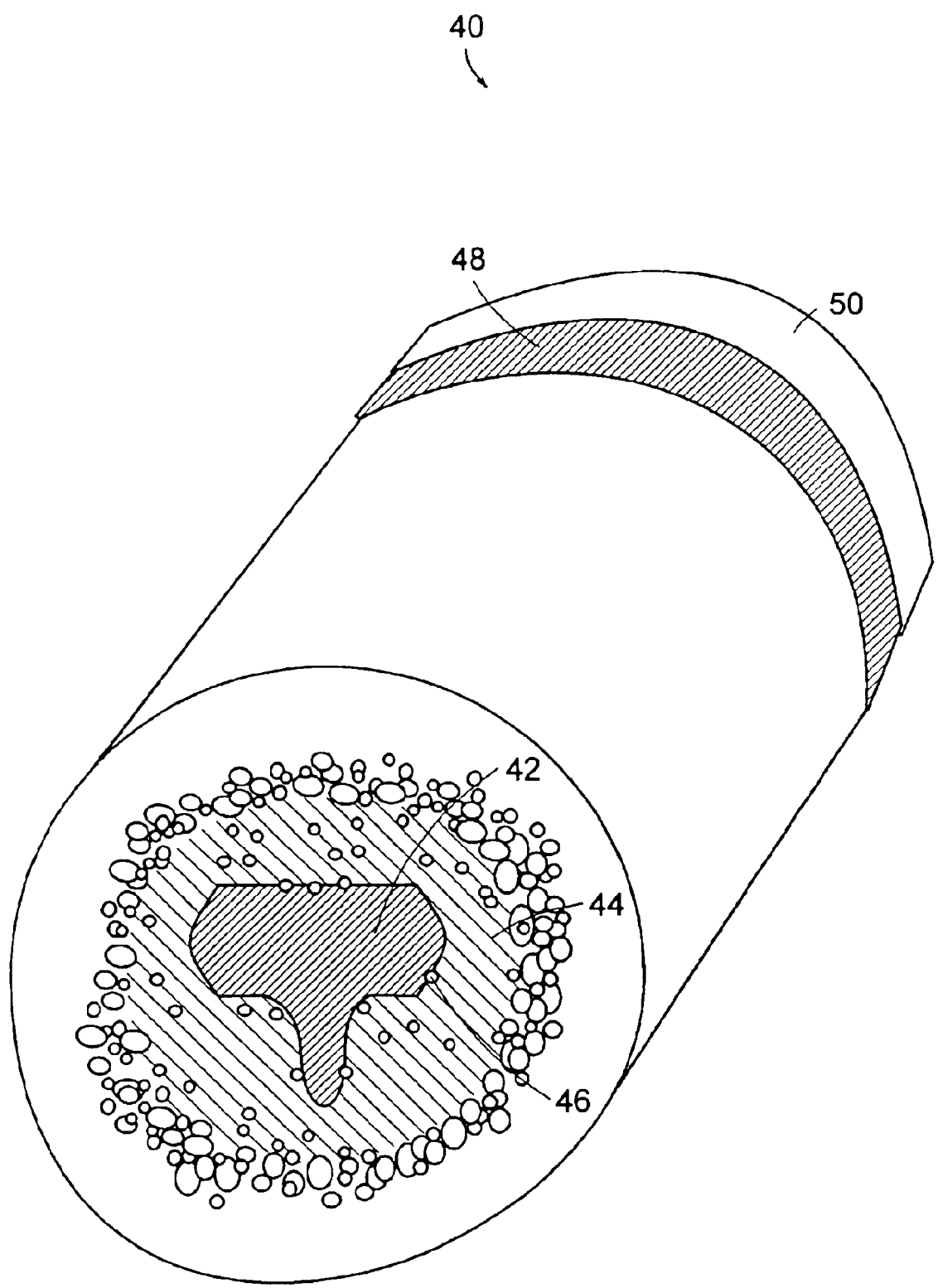
FIG. 2B is a schematic cross-sectional view of a knee implant using systems and methods in accordance with a preferred embodiment of the present invention.

Similarly, FIG. 2B is a schematic diagram of the distal portion of a tibia 40 after a knee arthroplasty showing in cross section the tibial stem component 42 of a joint prosthesis to the surrounding bone cement mantle 44 and pores 46 formed at the interface between the stem component and the bone cement.

Figure 3A:
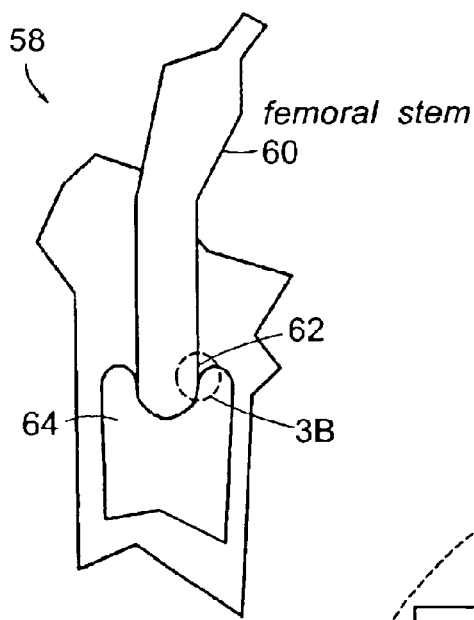
Figure 3B:
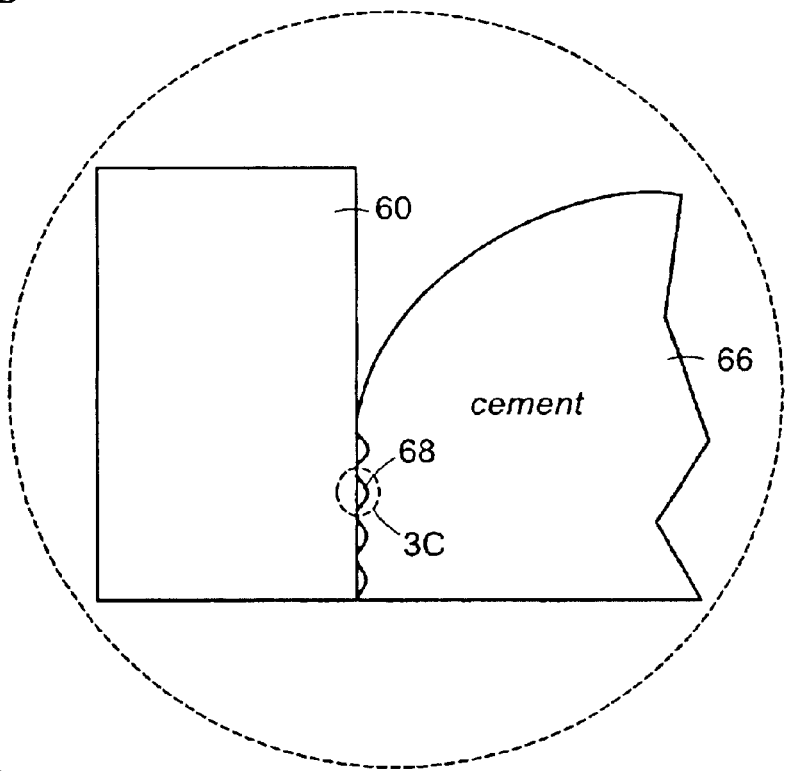
Figure 3C:
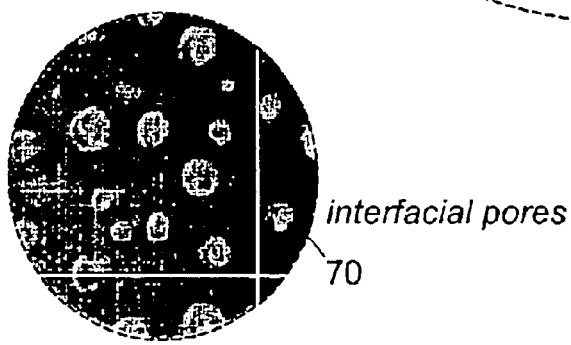

The interfacial pores are shown in FIGS. 3A–3B, which are diagrams of a longitudinal section of a femur 58 showing femoral stem component 60 during insertion into bone cement 64. The interface 62 between the stem component 60 and the bone cement 64 is shown in detail in FIGS. 3B and 3C. FIG. 3B shows interfacial pores 68 that are produced as the stem component 60 is inserted into the partially cured bone cement 66. FIG. 3C is a surface view of the interface between the stem component 60 and the bone cement 64 showing interfacial pores 70. In this figure, if the orthopedic stem component is inserted at a rate faster than the cement can spread on the surface of the stem component, which is related to its viscosity, pores are created along the cement-component interface.

Figure 4A:
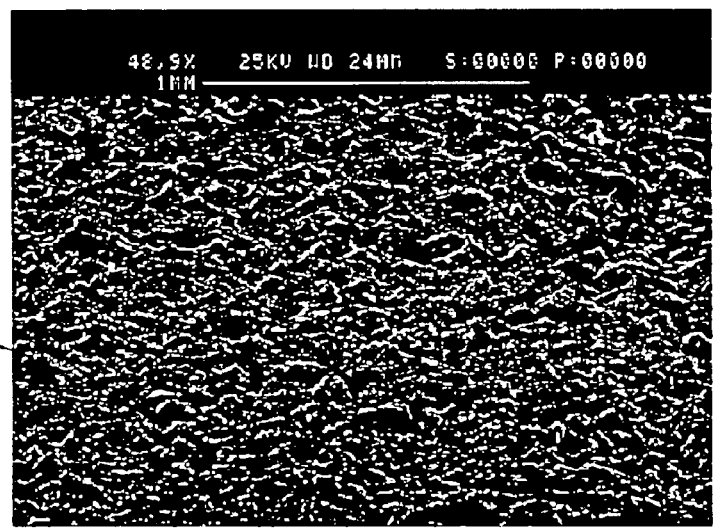
Figure 4B:
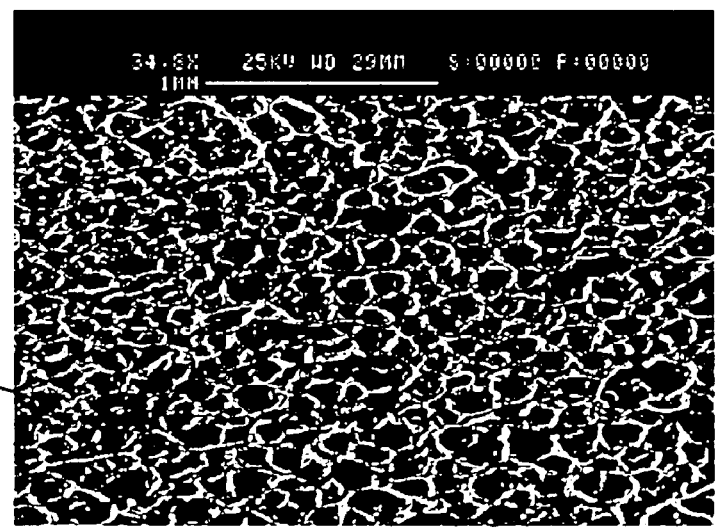

The number of interfacial pores depends on both the rate of insertion of the stem component and the viscosity of the bone cement. FIGS. 4A and 4B show surface views of the interface between the stem component and the bone cement as in FIG. 3C, imaged using a scanning electron microscope. FIG. 4A is a scanning electron micrograph (SEM) of the surface 80 of cured bone cement after a stem component is inserted relatively early during the cure process when the cement has relatively low viscosity. Few interfacial pores 82 are observed. In contrast, FIG. 4B is a SEM of the surface 90 of cured bone cement after a stem component is inserted relatively late during the cure process when the cement has relatively high viscosity. Many interfacial pores 92 are seen. The choice of insertion time relative to the viscosity during the progress of curing the cement is thus an important factor in the amount of interfacial porosity.

During the curing process of commercial bone cements, the dynamic viscosity can vary between 10 and $10^6$ Pascal-second. The viscosity additionally depends on the temperature at which the cements are mixed. Most commercial cements have a different formulation, and thus have a different viscosity-time profile. Consequently, the wetting behavior of the cements on an inserted prosthesis vary from cement to cement. One commonly used PMMA (polymethylmethacrylate) bone cement is, for example, Howmedica Simplex® P, which contains 75 weight percent (wt %) methyl methacrylate-Styrene-copolymer containing residual benzoyl peroxide, 15 wt % polymethylmethacrylate and 10 wt % barium sulfate. This bone cement is used in the systems and methods described below.

It has been found that the viscosity of partially cured bone cement can be reduced by applied shear forces due to the non-Newtonian characteristics of the partially cured bone cement. According to the present invention, oscillations imposed on the stem during insertion act to reduce the viscosity of the bone cement, resulting in the reduction of pores formed at the interface of the stem component and the cement.

Figure 5A:
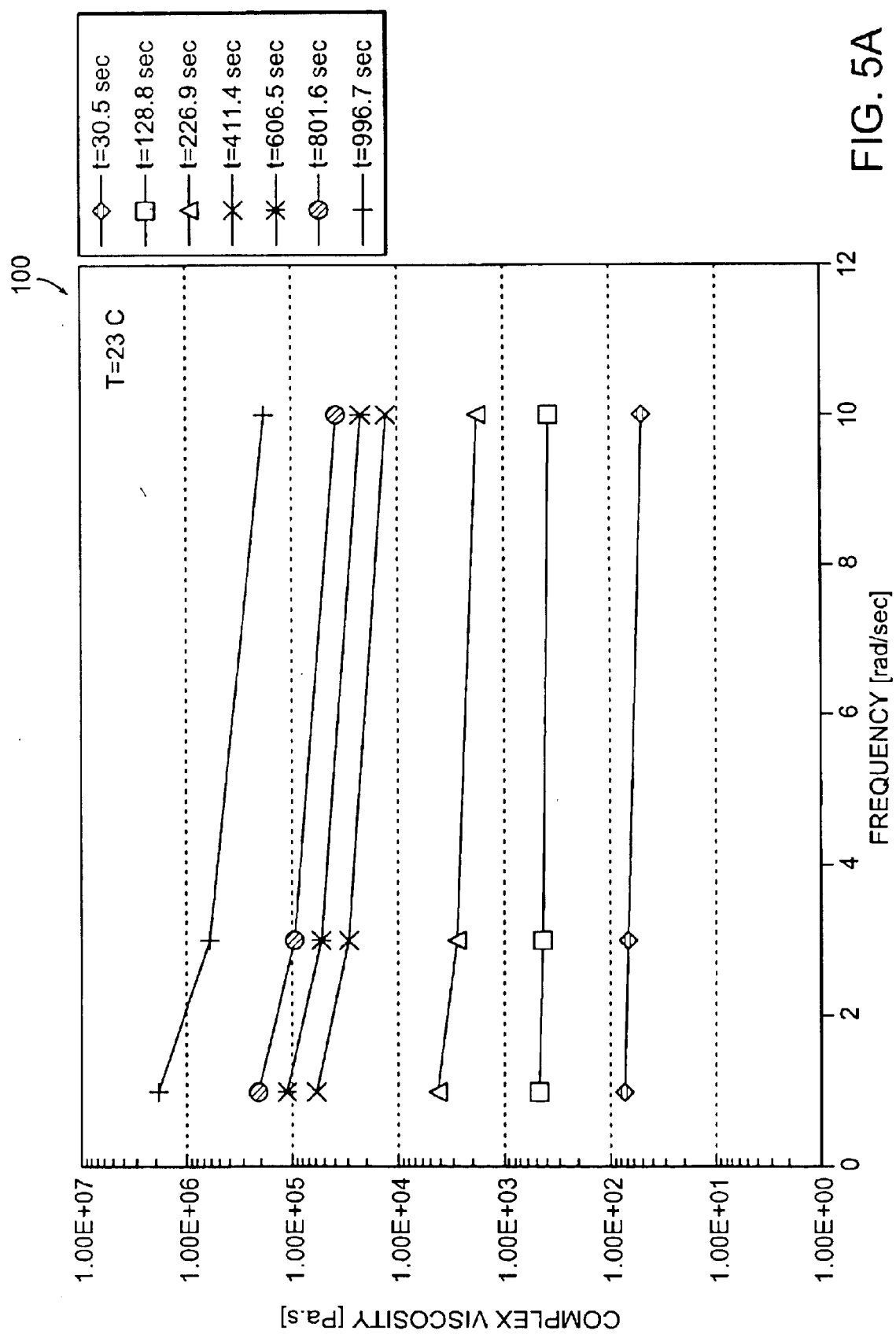
FIG. 5A graphically illustrates the relationship and dependence of complex shear viscosity of a bone cement structure on time after mixing and oscillating frequency, wherein the oscillating torque is 5,000 $\mu$N-m in accordance with a preferred embodiment of the present invention.
Figure 5B:
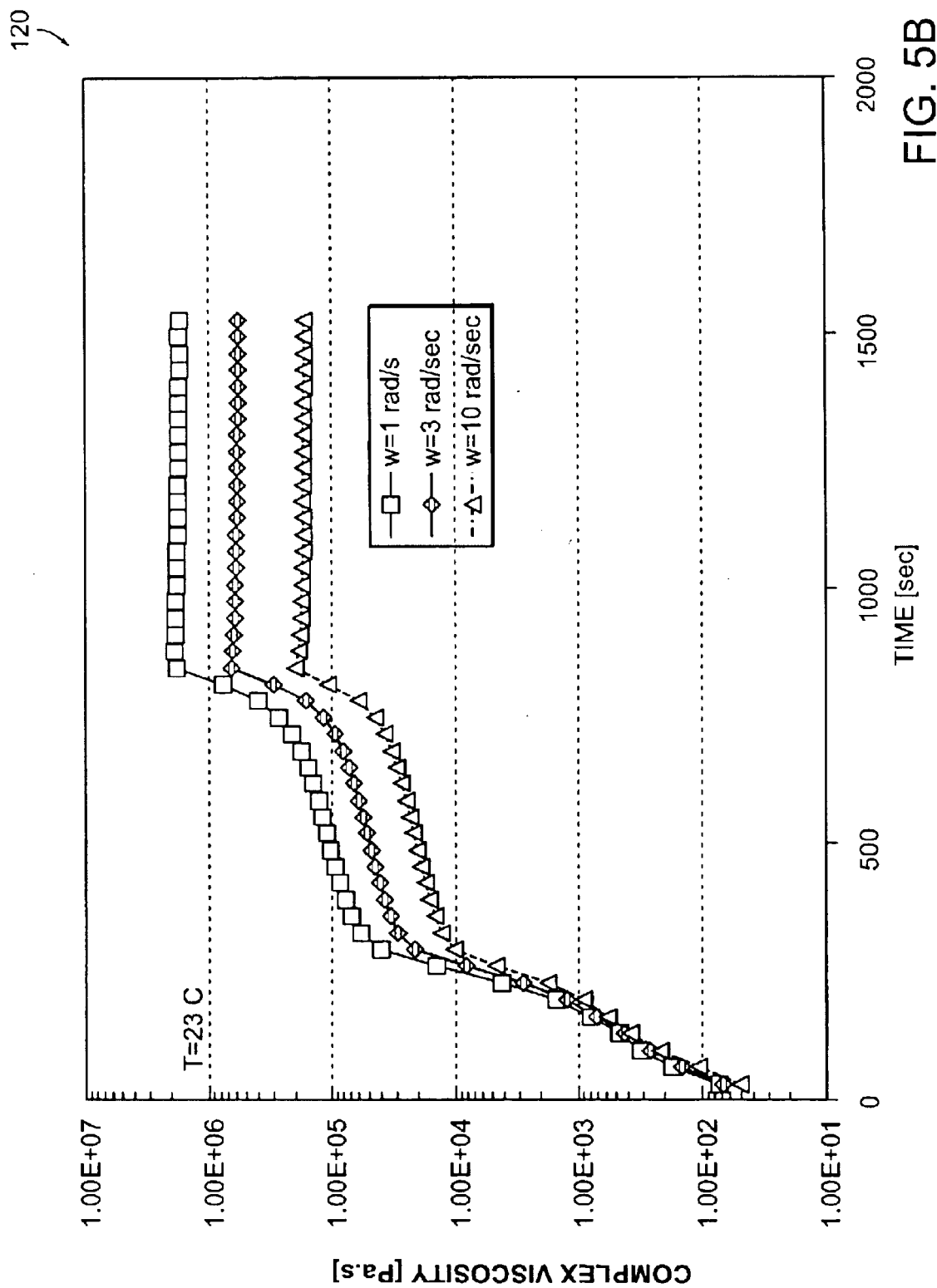
FIG. 5B graphically illustrates the relationship of complex shear viscosity with time as bone cement cures for data plotted in FIG. 5A in accordance with a preferred embodiment of the present invention.

In a preferred embodiment, using small amplitude oscillatory shear rheometry ot curing bone cements, there is a frequency dependence of the viscosity that is observed. In other words, as the frequency of the small amplitude oscillation increases, the viscosity of the cement decreases. FIGS. 5A and 5B show an example of this dependence as a function of cure time. FIG. 5A graphically illustrates the frequency dependence of complex shear viscosity in a family of curves 100 representing measurements taken in the cure process at succeeding times after mixing, using an oscillating torque of 5000 $\mu$N-m. Early in the curing process, when the cement has a lower viscosity, the dependence on the oscillating frequency is weak. As the cement begins to cure and becomes more non-Newtonian (i.e. more elastic-like versus viscous-like), the dependence on the frequency becomes more pronounced. Later in the cure, increasing the oscillating frequency from 1 to 10 rad/s decreases the viscosity by 85%. FIG. 5B graphically illustrates the same data as the complex shear viscosity as a function of cure time in a family of curves 120 representing oscillation at 1, 3 and 10 rad/sec in accordance with a preferred embodiment.

In preferred embodiments, the bone cement exhibits non-Newtonian rheological characteristics, in which the apparent viscosity is dependent on the shear rate applied to the composition. Preferably the bone cement has "shear-thinning" rheological properties. As used herein, "shear-thinning" refers to a reduction in apparent viscosity (the ratio of shear stress to the shear rate) with increasing shear rate, frequency, for example, the reduction in apparent viscosity can be time independent (pseudoplastic), time dependent (thixotropic) or associated with a yield stress, defined as a stress that must be exceeded before flow starts, for example, Bingham plastics and generalized Bingham plastics. The teachings generally in Harris, J., & Wilkinson, W. L., "Non-newtonian Fluid," pp.856–858 in Parker, S. P., ed., McGraw-Hill Encyclopedia of Physics, Second Edition, McGraw-Hill, New York, 1993 are incorporated herein by reference.

Figure 6:
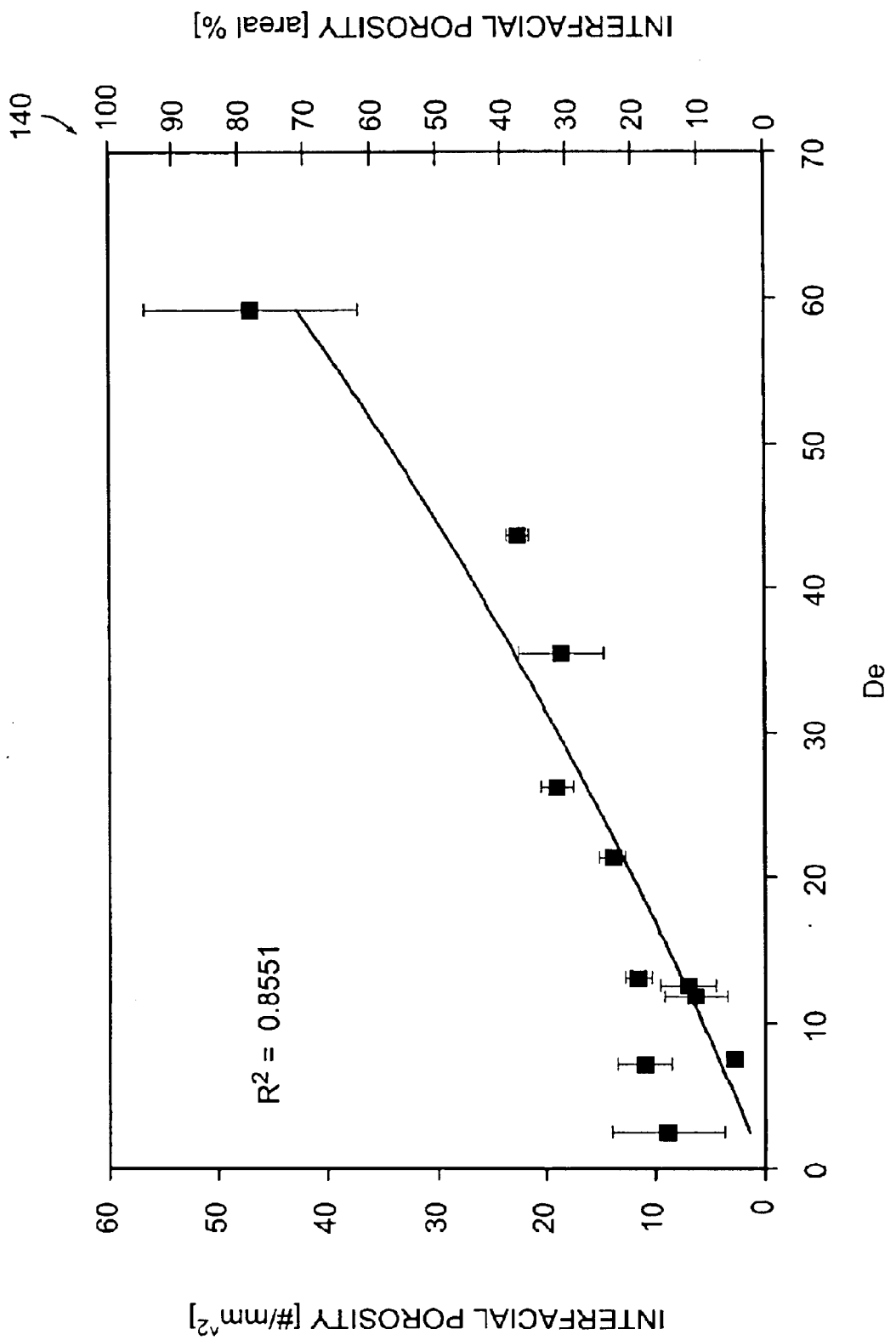
FIG. 6 graphically illustrates interfacial porosity as a function of Deborah number (De) which represents the ratio of bone cement relaxation time to shear rate during the insertion of a stem, in accordance with a preferred embodiment of the present invention.

FIG. 6 is a graphical illustration of the dependence of interfacial porosity on the Deborah number (De) of bone cement. A mean pore diameter of 150 $\mu$m is used. Deborah number (De) is the ratio of bone cement relaxation time to shear rate during the stem insertion. If the relaxation time is relatively long compared to the shear rate, the interfacial porosity is worse. Reducing the viscosity of the cement reduces the relaxation time, and thus the Deborah number. A lower Deborah number reduces the interfacial porosity down to the level of bulk porosity, for example, 7–10% for hand-mixed cement.

The system and method of the present invention takes advantage of the shear-thinning behavior of bone cement. Preferred embodiments of the invention include an actuator that controls a coupler which transmits energy to a prosthesis being inserted into the bone cement to reduce the interfacial porosity at the interface between the prostheses and the material. In one embodiment, a coupler device is attached to a metallic femoral stem. The coupler device has an internal oscillator which oscillates the stem at a prescribed frequency and amplitude, and in a specific direction. The frequency may be a series of overlaying frequencies. The vibrating stem is then inserted into the semi-cured bone cement in the bone cavity. This insertion can either be generated manually by the surgeon, or by a superposition of a steady extension and the oscillation signal on the oscillator drive. The drive signal can be generated by a linear motor or a combination of ball screw and hammer (or oscillation) mechanism. Any other suitable drive mechanisms can also be utilized. The oscillation may be electromechanical, piezoelectric, or any other suitable drive mechanism. The oscillation temporarily reduces the viscosity of the cement locally near the implant as it is inserted into the cavity, and thus reduces interfacial porosity.

One of the predicate of the systems and methods of the present invention are that a small amplitude oscillation locally reduces the viscosity of the cement, and hence aids in the wetting of the stem. However it can also be envisaged that a large amplitude, low frequency oscillation, whilst not affecting the viscosity markedly, may also improve the surface coverage. By oscillating the implant slowly, the implant can be repeatedly dipped slightly into the cement and then withdrawn. A thin precoat of cement may hence be dynamically applied to the stem, further improving the surface coating. If these two oscillation frequencies are superimposed over a steady insertion motion then the resulting signal concurrently precoats the implant and lowers the cement viscosity. The potential increase in implant/cement interface strength is considerable.

An added benefit of the bone cement viscosity reduction caused by the oscillation is that a lower amount of force required to insert the prosthetic stem into the cement-filled cavity. The reduced viscosity acts as a lubricating layer between the stem and the bulk cement mantle, reducing the shear stresses at this interface. A lower amount of required insertion force causes less trauma to the patient, and results in an easier procedure for the surgeon.

The time of insertion, as measured from the beginning of mixing, can vary between 2 minutes and the time to achieve a fully cured system, which can vary between 18–20 minutes. Earlier insertion benefits wetting, given that the cement is in a lower viscosity state. However, the cement can flow out of the reamed canal if insertion is performed too early. Additionally, pressurization of the cement, which allows the desired interpenetration of the cancellous bone, occurs best when the cement is in a higher viscosity state, i.e., when the stem is inserted at a later time. Conversely, a later insertion time yields poorer wetting and hence a worse interface between the prosthetic stem and cement. The preferred insertion times are between 3 and 15 minutes after the start of mixing, with a more preferred insertion time between 4 to 10 minutes, and a most preferred insertion time between 5 to 6 minutes. These times are for storage and mixing of the bone cement at room temperature. Different temperature changes these time.

Any of the embodiments, with minor modification, will have the ability to work with local positioning systems (LPS). In embodiments suitable for such automated applications, a LPS transceiver can be added to the system of the present invention to allow the surgeon to maintain alignment of the prosthesis during insertion. Further, the insertion system may be interfaced with a surgical robot to allow precise control over the insertion rate. Further embodiments combine an LPS transceiver with the robotic interface to allow precise control over both the alignment and insertion rate of the prosthesis.

In a preferred embodiment heating the stem before insertion into the cement-filled cavity results in reduced porosity at the cement-stem interface. Thus the reduction in porosity with heating resulted from changing the polymerization kinetics locally at the stem, the data analyzed and is ratified by consistent with the proposition that reduced viscosity, which arose from the increased temperature at the stem, results in decreased interfacial porosity. Some bone cements are known to have reduced viscosity at lower temperatures. Therefore, a preferred embodiment uses a generic active control of the stem temperature through a device such as, but not limited to, thermoelectric effect, water circulation. Preferred embodiments adjust the temperature of the stem before insertion, assuming slow equilibration once inserted. The viscosity of polymers typically show an Arhennius dependence (exponential) on temperature. Thus moderate changes of a few degrees can cause a decrease in viscosity by a factor of 20–50%. The prosthetic stem temperature is not be raised above the temperature where necrosis occurs at approximately 80 degrees Celsius. A stem temperature range between room temperature (20 degrees Celsius) and 60 degrees Celsius adequately reduces the viscosity of the cement in the region contacting the stem.

As an additional aid to reducing the viscosity locally, the stem component can be heated or cooled. This heating can occur via an inductive system, thermoelectrically, or via other methods that maintain the sterile conditions of the orthopedic components. The temperature range can be about 4 degrees Celsius to about 60 degrees Celsius. To heat a typical femoral stem component from room temperature up to 40 degrees Celsius in 10 minutes, approximately 6 W of power is required.

A critical problem in orthopedic surgery is determining when the cement is at the desired cure level. In a procedure this information is obtained either using the cure time, or, more normally, by a tactile test where the surgeon determines its condition by experience and feel. In a preferred embodiment the addition of a force sensor (transducer) to the vibration system allows the determination of the cement viscosity in real time. By coupling the implant to the cement surface before insertion the cement viscosity can be determined because the displacement (and hence strain) is known (programmed) and the force (and hence stress) is known (from the force sensor). This provides the surgeon with a clear indication of the optimum time for insertion. This can be based on the relationship describing the connection between stress and strain:

$$\eta^* = \frac{\tau^*}{\dot{\gamma}} = \eta' + i\eta''; \eta' = \frac{\tau_o''}{\dot{\gamma}_o}; \eta'' = \frac{\tau_o'}{\dot{\gamma}_o} \qquad \text{Equation 1}$$

By knowing the complex stress ($\tau^* = \tau' + i\tau''$) and shear rate ($\dot{\gamma}$) which are related to force (F) and velocity (v) through the area of interaction (A) and a characteristic length (h)

$$\tau = \frac{F}{A}; \dot{\gamma} = \frac{v}{h} \qquad \text{Equation 2}$$

Alternatively the magnitude of the complex viscosity can also be used. Alternatively, when the force has reached a pre-determined optimal level, the system allows either automatic or manual insertion of the prosthesis.

To characterize the typical insertion force required to drive a stem into typical bone cement, a simple-superimposed couette-poiseuille velocity profile may be used to obtain the shear rates. The velocity profile for cement extruded by stem insertion:

$$v(y) = y\frac{v_s}{h} - \left[\frac{6Q}{h}\right]\left[\frac{y}{h} - \left(\frac{y}{h}\right)^2\right] \qquad \text{Equation 3}$$

where y is the dimension in the gap between the stem and bone (where the cement is flowing), h is the gap width, Q is the normalized flux due to cement displacement by the stem, and $v_s$ is the velocity of the stem. Using this expression, flow in a channel is assumed which varies minimally from flow in confined to a concentric gap (the geometry of a typical hip cement space). To derive the shear rate at the stem interface this expression is differentiated to obtain:

$$\frac{dv}{dy} = \frac{v_s}{h} - \left[\frac{6Q}{h}\right]\left[\frac{1}{h} - \left(\frac{y}{h^2}\right)\right] \qquad \text{Equation 4}$$

Evaluation of this expression at y=0 and multiplying by the viscosity of the cement gives the shear stress on the stem:

$$\tau = \mu\frac{dv}{dy}\bigg|_o \qquad \text{Equation 5}$$

where τ, is the shear stress and µ, is the cement viscosity. To obtain the maximum insertion force necessary to drive a hip stem into the cement, the shear stress, τ, is multiplied by the stem area:

$$F = \tau d\pi l \qquad \text{Equation 6}$$

where d is the diameter of the stem and l is the length.

In a preferred embodiment, Howmedica Simplex P®, cured for 6 minutes, using a six inch simulated stem, and inserting at 1 cm/sec with no oscillation is used and the maximum insertion force is approximately 200 newtons. In contrast, if the stem component is oscillated at 10 rad/sec, taking advantage of the reduction in viscosity due to the shear-thinning characteristics of the bone cement, the maximum insertion force is approximately 100 newtons. Thus, the force required to insert a hip stem is substantially reduced using the system and method of the present invention.

The method and device in a preferred embodiment exploits the shear-thinning rheologic behavior of bone cement. In one embodiment, an actuator having a coupler is attached to a metallic femoral stem. The actuator with the coupler has an internal oscillator which oscillates the stem at a prescribed frequency and amplitude, and in a specific direction. The frequency may be a series of overlaying frequencies. The vibrating stem is then inserted into the semi-cured bone cement in the bone cavity. This insertion can either be generated manually by the surgeon, or by a superimposition of a steady extension and the oscillation signal on the oscillator drive. The drive signal can be generated by a linear motor or a combination of ball screw and hammer (or oscillation) mechanism. Any other suitable drive mechanism can also be utilized. The oscillation may be electromechanical, piezoelectric, or any other suitable drive mechanism. The oscillation temporarily reduces the viscosity of the cement locally near the implant as it is inserted into the cavity, and thus reduces interfacial porosity.

A small amplitude oscillation locally reduces the viscosity of the cement, and hence aids in the wetting of the stem. However it can also be envisaged that a large amplitude, low frequency oscillation, whilst not affecting the viscosity markedly, improves the surface coverage. By oscillating the implant slowly, the implant is repeatedly dipped slightly into the cement and then withdrawn. A thin precoat of cement may hence be dynamically applied to the stem, further improving the surface coating. If these two oscillation frequencies are superimposed over a steady insertion motion then the resulting signal concurrently precoats the implant and lowers the cement viscosity. The potential increase in implant/cement interface strength is considerable.

Figure 7:
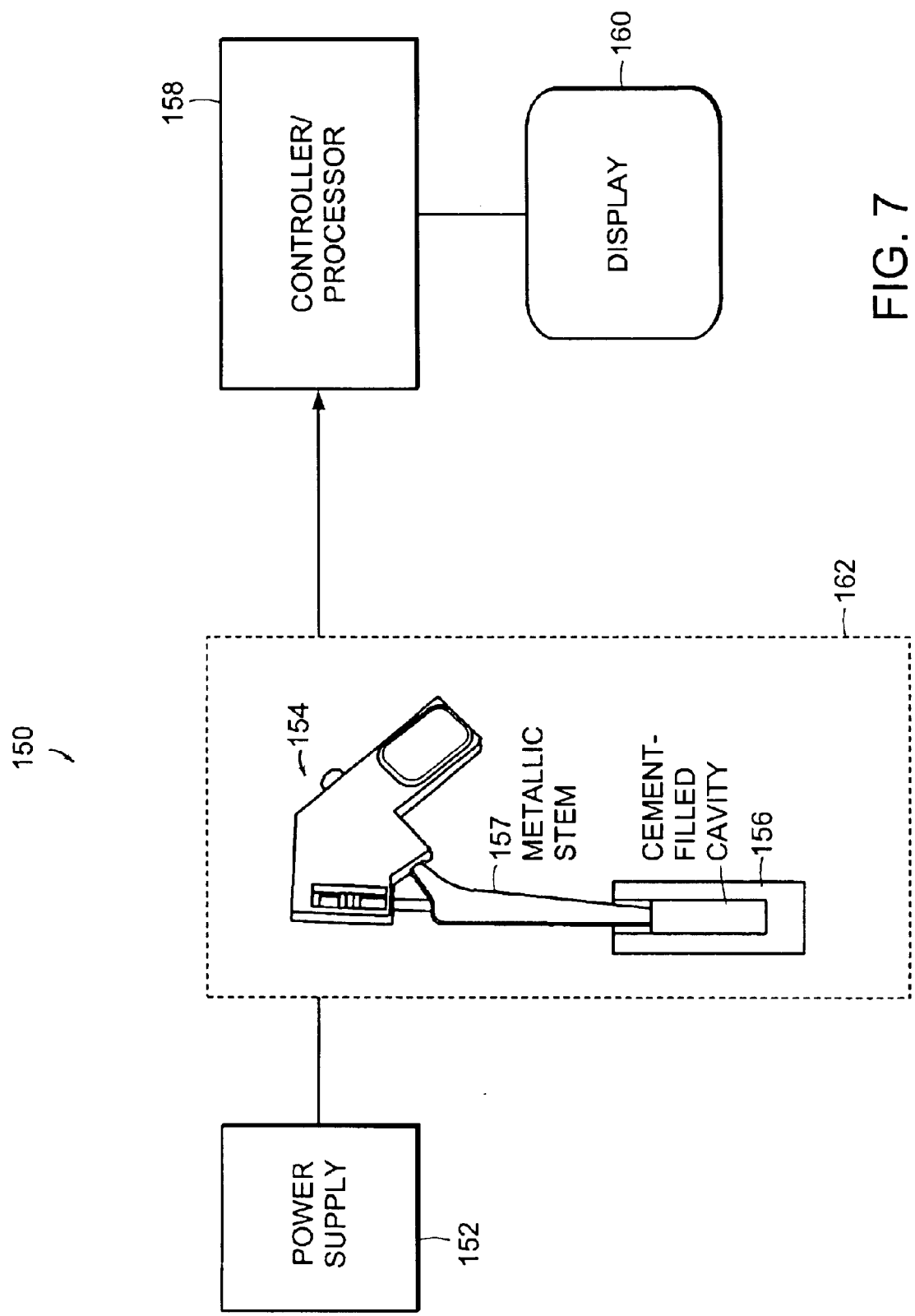
FIG. 7 is a schematic illustration of a system used to implant an orthopedic component, in accordance with a preferred embodiment of the present invention.

A preferred embodiment of the present invention provides a system including an oscillatory actuator for implanting a metallic component in a non-Newtonian cement. One embodiment is illustrated schematically in FIG. 7. The system 150 includes a power supply 152, hand-held insertion device 154, controller/processor 158, and a display 160. The environment 162 in which the hand-held device 154 is used includes a metallic stem component of a orthopedic prosthesis 157 to be inserted into a cement-filled cavity in a bone 156.

Figure 8A:
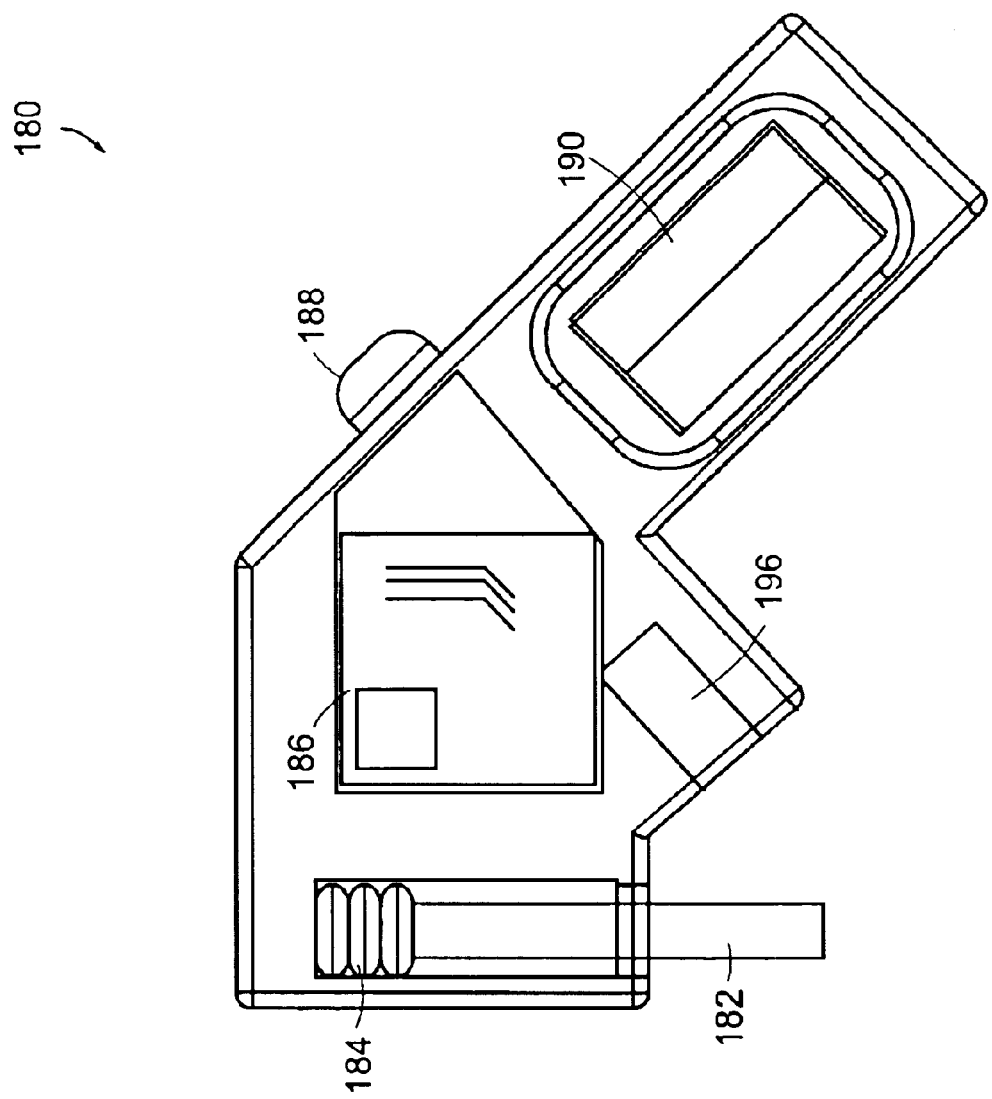
FIGS. 8A and 8B are schematic diagrams of an insertion apparatus used in systems for implanting orthopedic components in accordance with a preferred embodiment of the present invention.
Figure 8B:
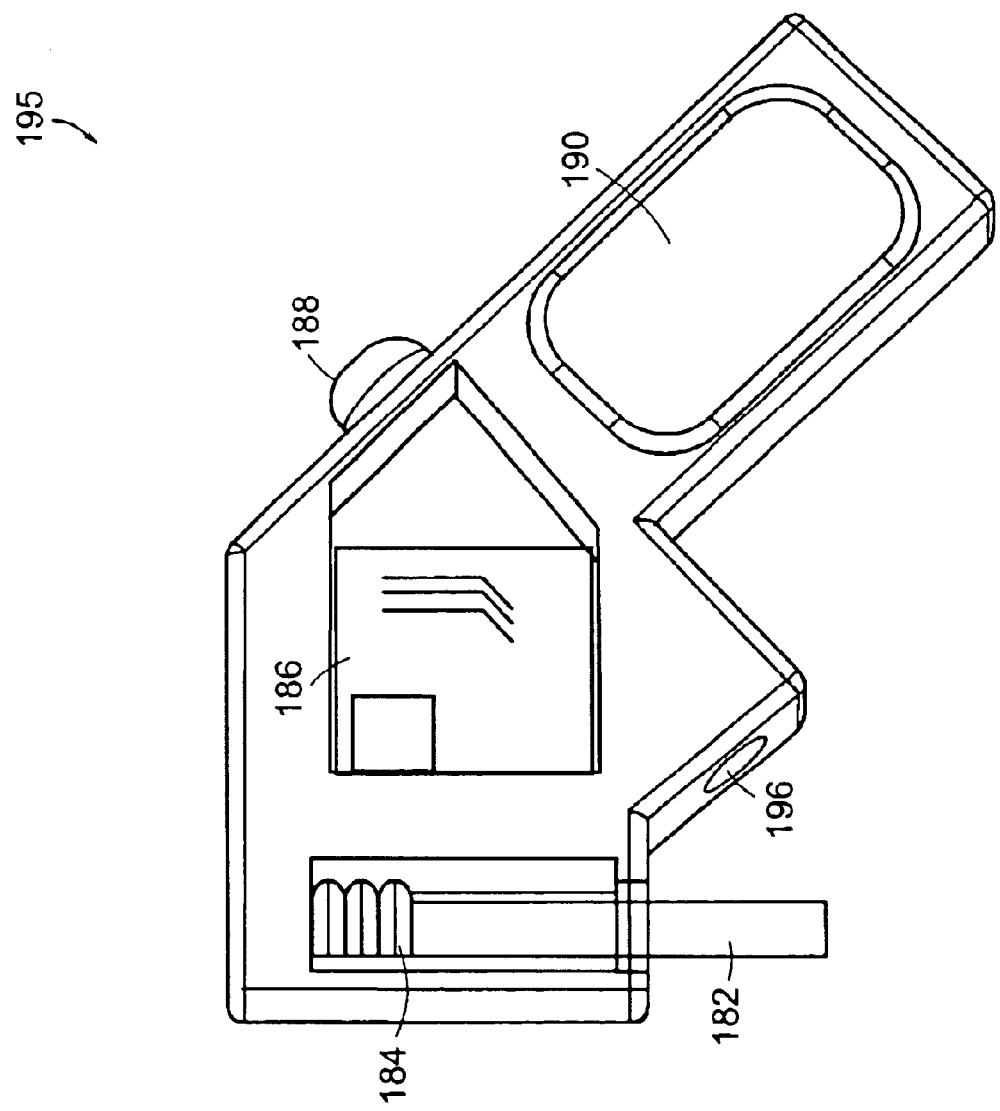

An embodiment of the hand-held insertion device is shown in the schematic diagrams of FIGS. 8A and 8B. In FIG. 8A, the hand-held insertion device 180 includes an oscillation member 182 driven by an oscillation actuator 184. A stem component recess 196 is defined by the housing of the hand-held insertion device 180. An electronic circuit board 186 is electrically connected to a control circuit having a control switch 188 and a battery pack 190. FIG. 8B provides a three dimensional view of the hand-held insertion device 195, showing oscillation member 182 driven by an oscillation actuator 184 a stem component recess 196 defined by the housing of the hand-held insertion device, an electronic circuit board 186, electrically connected to a control switch 188 and a battery pack 190.

Figure 9A:
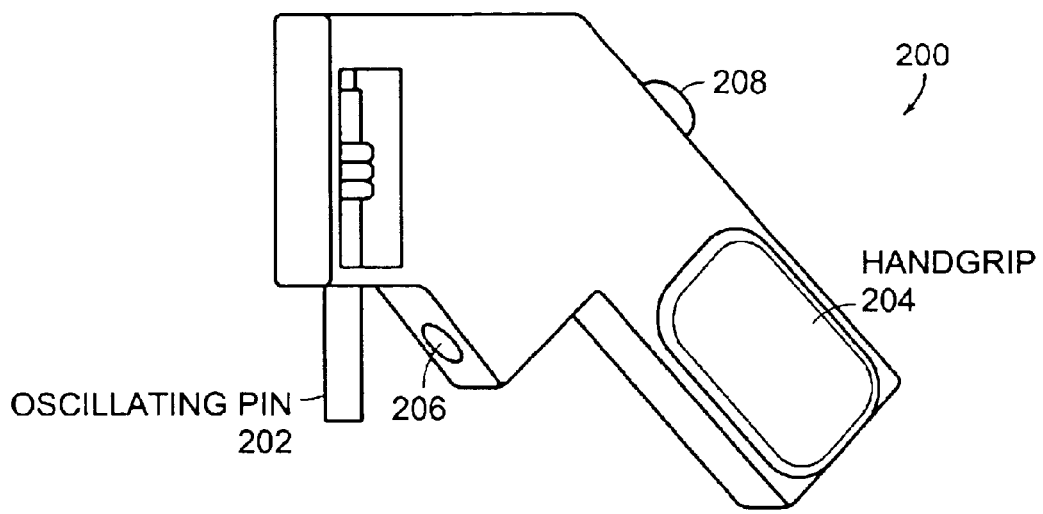
FIG. 9A is a three dimensional schematic view of an insertion apparatus in accordance with a preferred embodiment of the present invention.
Figure 9B:
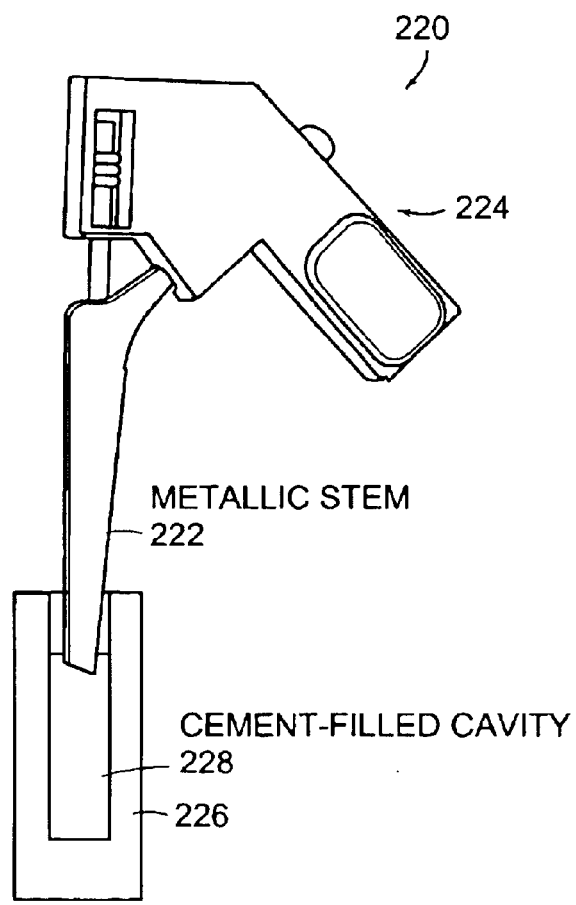
FIG. 9B is a three dimensional schematic view of an insertion apparatus being used for an orthopedic implant in accordance with a preferred embodiment of the present invention.
Figure 9C:
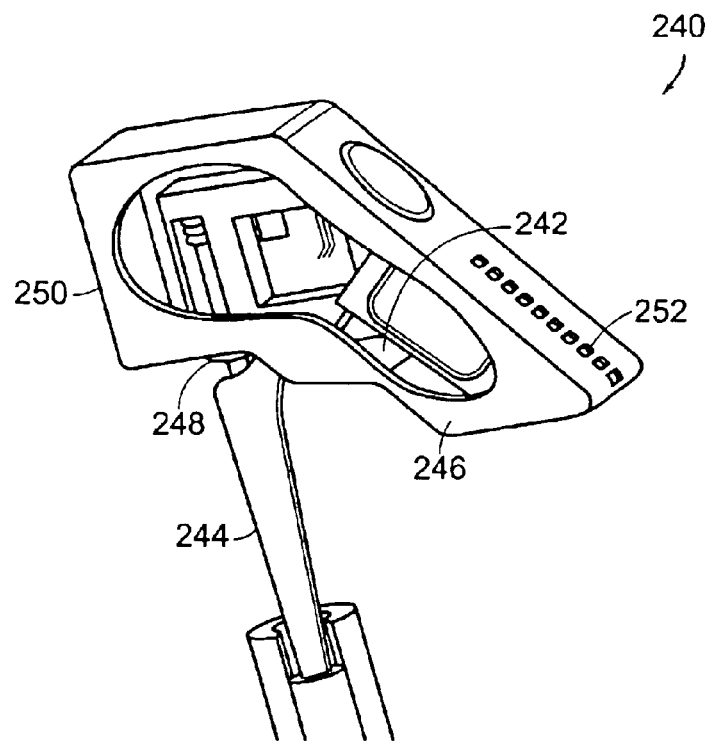
FIG. 9C is a detailed three dimensional schematic view of an insertion apparatus coupled to an orthopedic stem in accordance with a preferred embodiment of the present invention.

Another three-dimensional view of a preferred embodiment of the hand-held insertion device is shown schematically in FIG. 9A. The hand-held insertion device 200 includes an oscillation member, or "oscillating pin", 202, a stem component recess 206 defined by the housing of the hand-held insertion device 200, a control switch 208 and a handgrip 204. FIG. 9B illustrates diagrammatically the use of an embodiment of the hand-held insertion device 224 coupled to a metallic stem component 222 inserted into a cement-filled cavity 228 of a bone 226. FIG. 9C illustrates diagrammatically the use of an embodiment of the hand-held insertion device 240 coupled to a metallic stem component 244. The entire hand-held insertion device 240 is contained in a hermetic bag 246 that is connected to the metallic stem component 244 and the oscillation member through sterile pass-through ports, such as 248. The flexible sterile sheath or bag is shown with a schematic cut-out 250. The device is placed in the bag through a hermetic zip-lock mechanism 252. The conformable bag 246 allows easy handling of the apparatus, and can be sterilized or can be made disposable.

Figure 10:
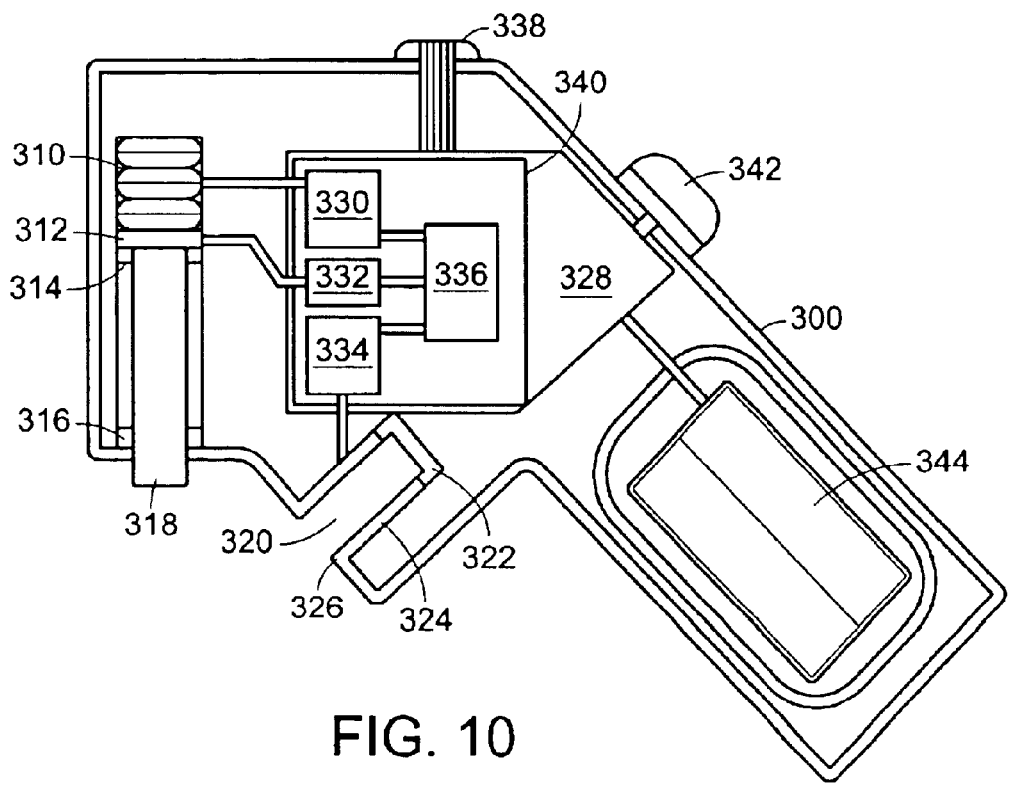
FIG. 10 is a detailed schematic view of an insertion apparatus in accordance with a preferred embodiment of the present invention.

With reference to the schematic diagram of FIG. 10, in a preferred embodiment the system includes a hand-held device 300 that includes an oscillation actuator 310, a stem component recess 320 defined by a cap 322, a heating element 324 and a retaining ring 326, and electronic circuitry 328.

The oscillation actuator 310 is mechanically coupled to a force transducer 312 that is in turn is mechanically coupled to an oscillation member 318. Suitable bearings 314 and 316 restrict the lateral movement of the oscillation member 318.

The electronic circuitry 328 is electrically connected to a control and monitoring module 340, an input/output connector 338, a switch 342, and a battery pack 344. The control and monitoring module 340 includes an oscillation actuator controller 330 electrically connected to an electronic controller 336 that is in turn electrically connected to force transducer controller 332 and heater controller 334. The force transducer controller 332 is electrically connected to the force transducer 312. The input/output connector 338 provides electrical connections to an external display for monitoring the values of insertion force, oscillation amplitude or oscillation frequency, to an external power supply that provides power to the heater. The switch 342 is preferably a multifunction switch similar to those found on video game control pads, and provides the surgeon with thumb-tip control of at least one parameter selected from the group consisting of stem component temperature, oscillation amplitude or oscillation frequency. In a preferred embodiment, switch 342 provides the surgeon with thumb-tip control of at least two parameters selected from the group consisting of stem component temperature, oscillation amplitude or oscillation frequency. The battery pack 344 provides power to the electronic circuitry 328, and provides the ability to power the oscillation actuator 310 in the event of disconnection from or failure of the external monitor. In a preferred embodiment the heater 324 is a Peltier cell that provides the ability to heat or to cool the stem component. In some alternative embodiments heater 324 is an electrical resistance heater. In other alternative embodiments heater 324 is a heat exchanger through which heated or cooled fluid is circulated.

Figure 11A:
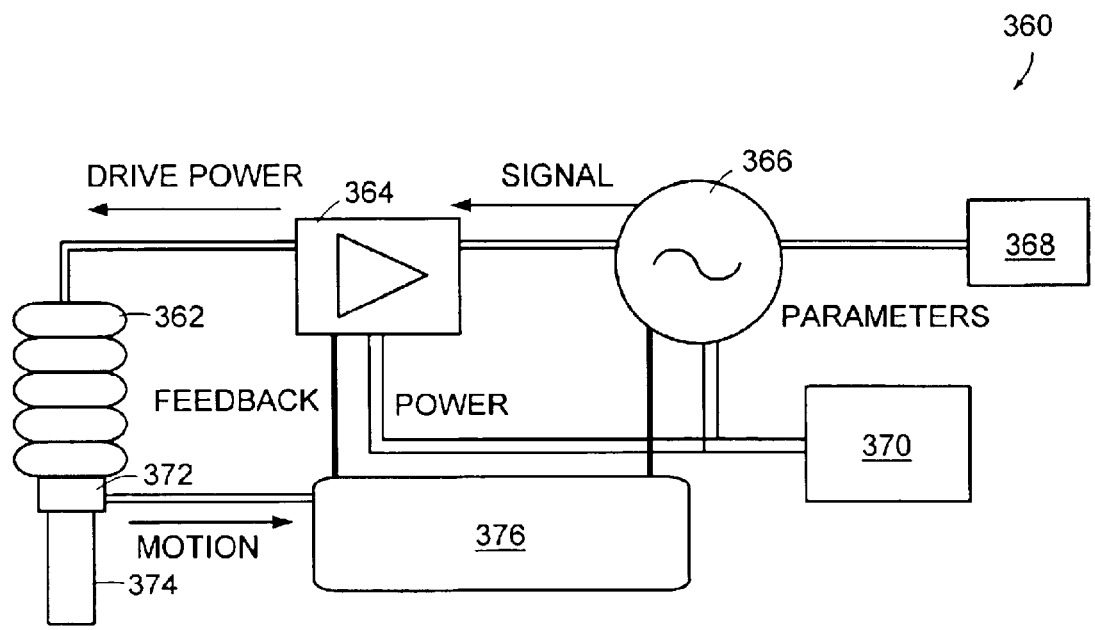
Figure 11B:
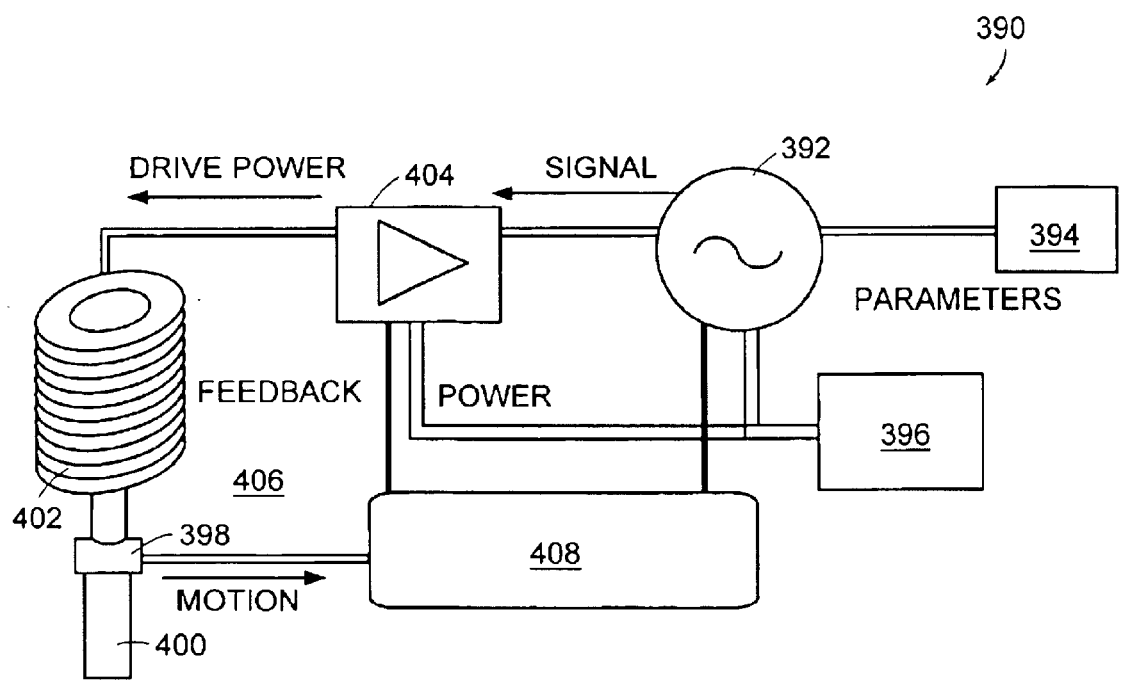

FIGS. 11A and 11B show schematic diagrams of two embodiments of drive systems suitable for the oscillation actuator. FIG. 11A illustrates a piezoelectric based system 360 where the piezo stack 362 is a piezoelectric ceramic tube, or a stack of piezoelectric ceramic tubes, or any other configuration capable of generating the required displacement and force. The piezo stack 362 is driven by a high voltage, low current amplifier 364 that receives the oscillator signal from an oscillator circuit 366 that has adjustable parameters. The oscillator circuit 366 can be a simple analogue oscillator or alternatively be a digital signal processing system. The parameters can be set in an external module 368 that in one embodiment comprises a switch to allow selection of suitable parameters appropriate for each different cement. In a preferred embodiment, the external module 368 comprises a removable "card" that contains the parameters stored either in digital memory or in a network of resistors, capacitors and inductors. This removable card can be transported individually with each cement to ensure that the correct parameters are tied to the correct cements. The oscillator circuit 366 and the amplifier 364 are powered by a power supply 370, which is in some embodiments a battery contained within the hand-held insertion device, or alternatively the system power supply. The motion information is fed back to a processing block 376 that adjusts the gain of the amplifier 364 and the frequency and shape of the output of the oscillator circuit 366 as necessary.

FIG. 11B illustrates an electromagnetic based system 390 having an electromagnetic coil 402 and a ferrous driving rod 406. This electromagnetic coil 402 is driven by a high current, low voltage amplifier 404 using signals derived from the same components as above (oscillator 392, parameters 394 and power supply 396). In a preferred embodiment an accelerometer 398 is mounted between the ferrous driving rod 406 and the shaft of the stem component 400 to provide feedback to the circuit, allowing the circuit to adapt if energy transfer is not optimal. In some preferred embodiments the accelerometer 398 also contains a force sensor to provide information about the cement condition. The acceleration and/or force information is fed back to a processing block 408 that adjusts the gain of the amplifier 404 and the frequency and shape of the output of the oscillator circuit 392 as necessary.

Figure 12C:
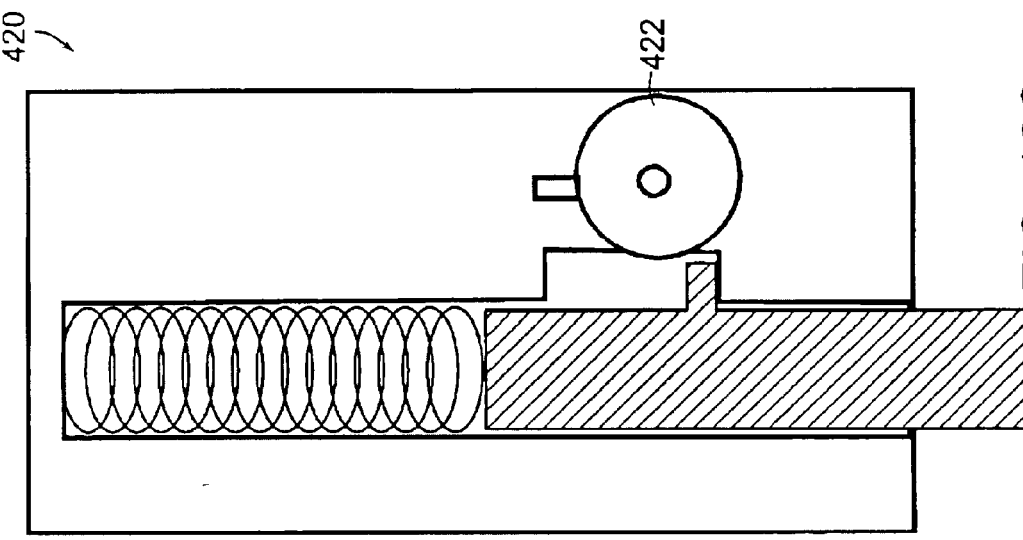
FIGS. 12A–12C are schematic diagrams of an alternate preferred embodiment of a system using a vibration subsystem to insert an orthopedic component in accordance with the present invention.
Figure 12B:
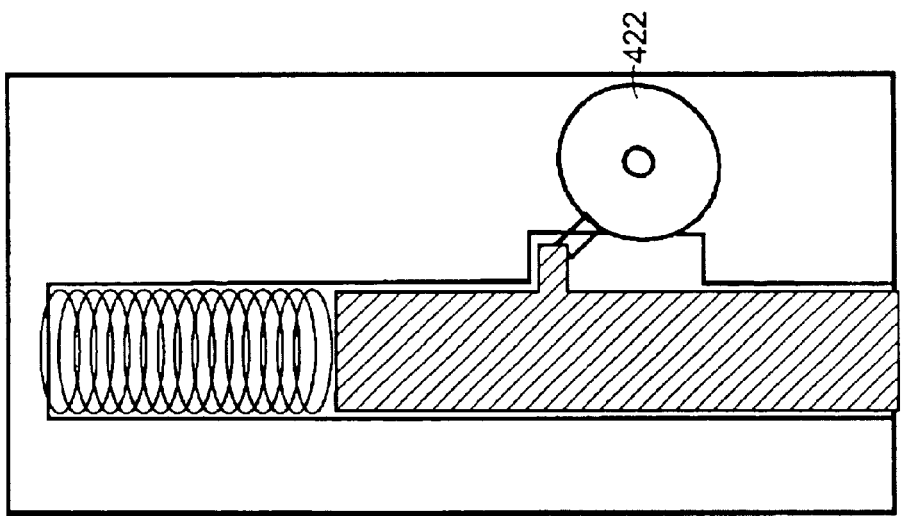
Figure 12A:
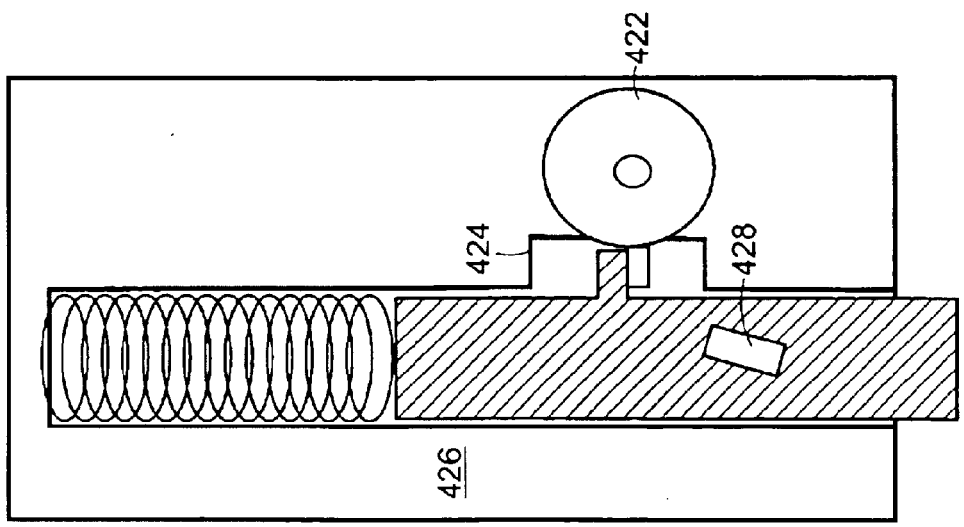

FIGS. 12A–12C are schematic illustrations of an alternate embodiment of an oscillation actuator 420. A rotating wheel 422 with a radially-mounted tab contacts the lever arm 424 of the oscillating member 428. The tab pushes the oscillating member 428 upwards against the spring 426 lifting the prosthesis with it. When the rotating wheel 422 moves beyond 45 degrees, the lever arm 424 is released, and the spring 426 pushes the oscillating member 428 and prosthesis down according to the prescribed throw. When the wheel completes the 360 degree rotation, the process repeats. The frequency is dictated by the speed of the motor attached to the rotating wheel 422.

Figure 13:
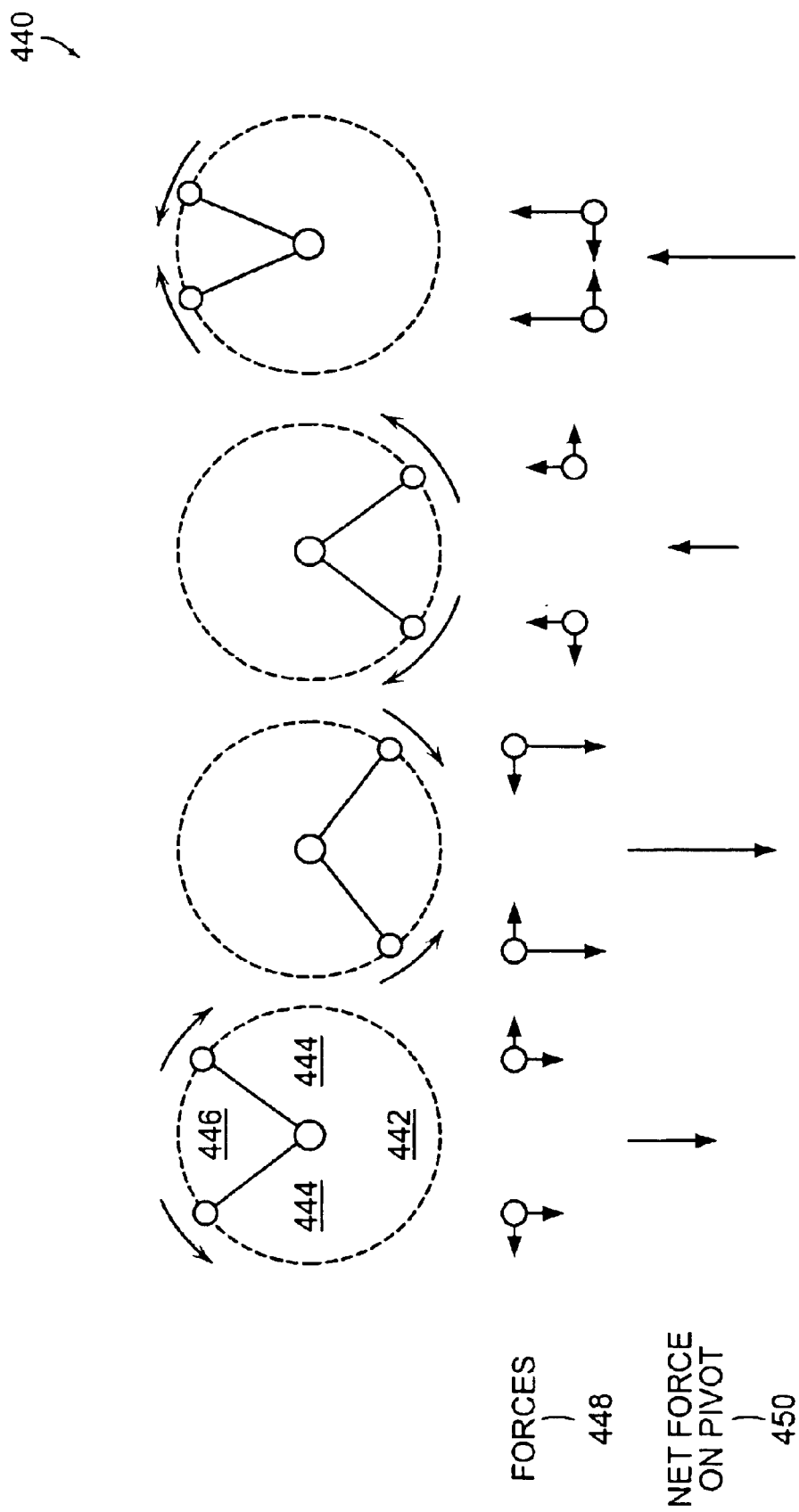
FIG. 13 is a schematic representation of a drive subsystem used in a system to insert orthopedic components in accordance with a preferred embodiment of the present invention.

FIG. 13 is a schematic illustration of an alternate embodiment of an oscillation actuator 440. A hub 442 is driven by some suitable rotary motion. This motion can be from compressed air or from and electric motor or from any other suitable actuator. The hub is mounted to two masses 444 via pendulum arms 446. The hub is mounted through a gearing system that allows contra-rotation. Thus as the hub rotates the masses move in opposition. The vectoral forces on the masses therefore act to provide uniaxial force in the vertical direction and no force in the horizontal direction. Frequency of oscillation of the hub can be controlled by the hub rotational velocity and amplitude can be controlled by the position of the masses 444 on the pendulum arms 446.

FIG. 14A is a schematic illustration of an alternate embodiment of an oscillation actuator 460. Any suitable rotary drive may be used (such as pneumatic or an electric motor) to drive a cam 462 that can have any arbitrary shape with, or without an offset shaft. The shape is chosen appropriate for a particular oscillation profile. This rotating cam 462 drives through a line contact an oscillation member 464 that contacts to the implant stem component. This oscillation member 464 is connected through a spring 466 to the body of the unit 468 to which the driving motor and hub are also attached. The spring 466 ensures that the oscillation member 464 and hence the stem accurately follow the motion of the cam 462.

FIG. 14B is a schematic illustration of an alternate embodiment of an oscillation actuator 480. Any suitable reciprocating drive can be used. In this embodiment a reciprocating drive 482 is mounted rigidly on a frame 490. The moving tip of the drive is mounted to a coupler 484 which allows connection of the implant stem. This coupler is mounted to the frame 490 through a spring 486 and damper 488 system that allows tuning of the shape of the curve. By careful choice of damper/spring system the on-off motion of the drive 482 can be smoothed to a more suitable curve. The drive 482 could be an electromagnetic based system such as a solenoid or it could be such a system as described in the figure. Here a piston 494 has a relief valve 492. At step (I) in the figure the piston is at the home position and the relief valve is closed. As the air pressure builds the drive proceeds through step (II) until step (III) is reached where the internal pressure exceeds the relief valve pressure, the valve opens and the piston returns to home (I).

Figure 15:
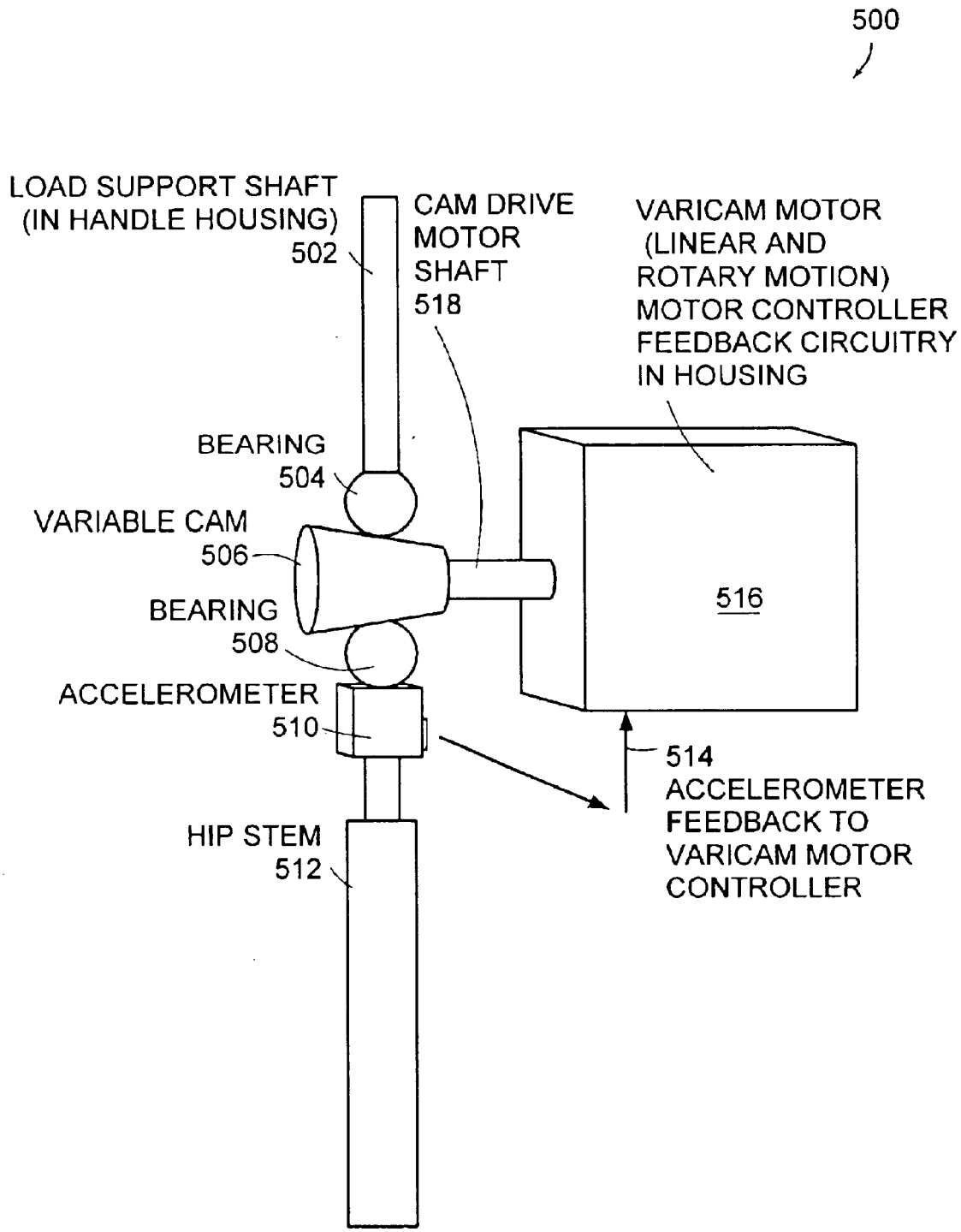
FIG. 15 schematically illustrates a varicam system to modulate the oscillatory amplitude to a prosthesis in accordance with a preferred embodiment of the present invention.

FIG. 15 is a schematic illustration of an alternate embodiment of an oscillation actuator 500 based on a variable cam system for controlling oscillatory amplitude. In practice, the actual amplitude of oscillation of the hip prosthesis depends not only on the applied displacement of the prosthesis from the insertion tool, but on the ratio of the reaction force of the insertion tool and the reaction force of the bone cement and hip prosthesis. The reaction force of the insertion tool is a function of the inertia of the tool itself plus the force applied by the surgeon during insertion. To compensate for the variability of the latter, the insertion device, in all embodiments, utilize a feed back control system that modulates the amplitude of the applied oscillatory motion.

In this preferred embodiment, to control the amplitude of oscillations of the hip stem a variable cam system is proposed. An accelerometer 510 is used to sense the oscillation of the stem component 512 as it is inserted. If the amplitude of the oscillatory motion does not fall within the prescribed criteria for the current insertion, then the feedback signal 514 to the control circuitry in the varicam motor controller 516 actuates the linear driver in the varicam motor. The varicam 506 is linearly translated to either increase or decrease the amplitude of the oscillation to compensate for the error in the feedback signal.

Figure 16:
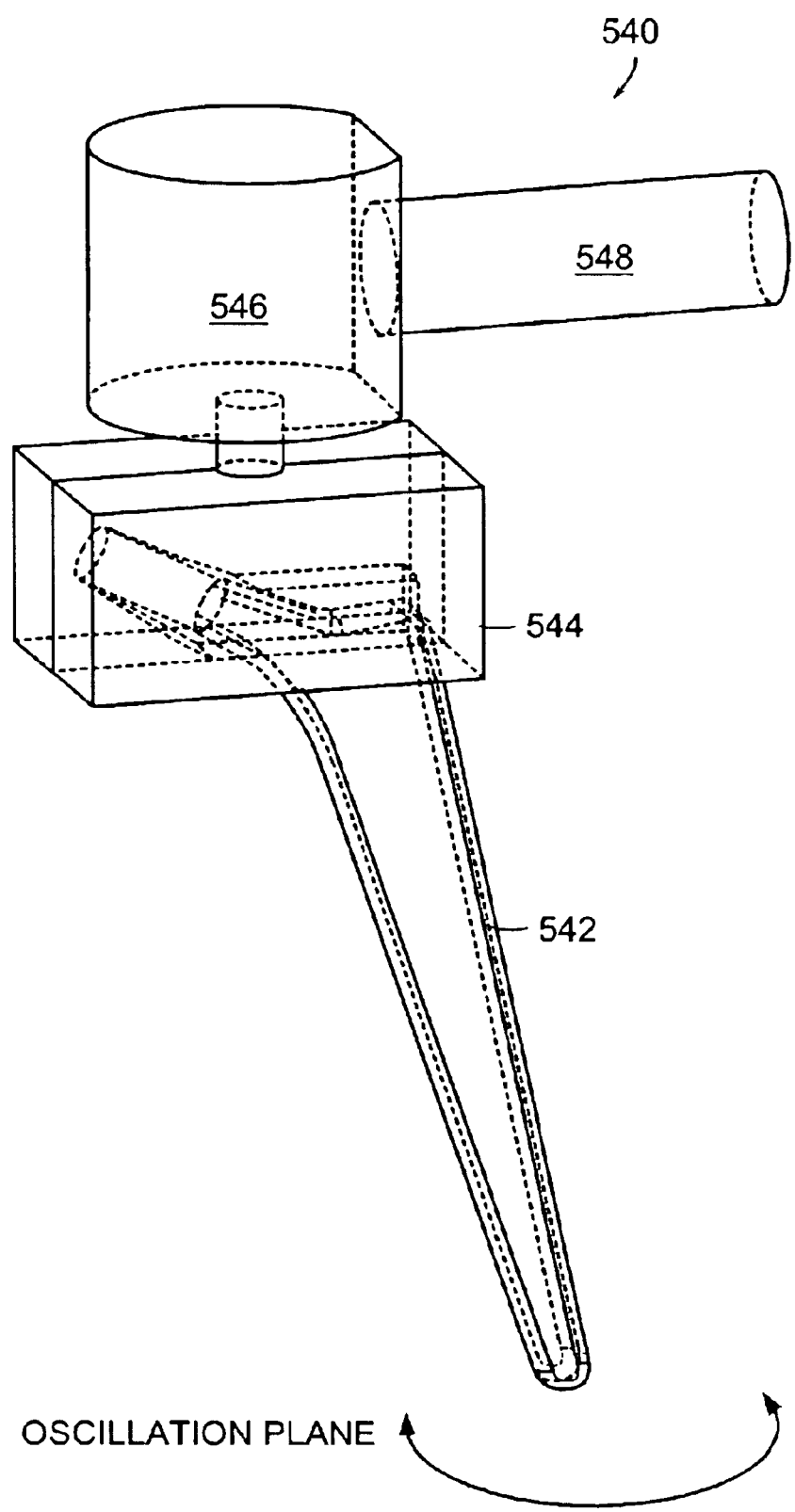
FIG. 16 schematically illustrates a drive system based on rotational vibration in accordance with a preferred embodiment of the present invention.

FIG. 16 is a schematic illustration of an alternative preferred embodiment with a drive system based on a rotational vibration. The stem component of the prosthetic implant 542 is gripped in the block 544. A stepper motor 546 is rigidly attached to the block 544. The stem vibrates with a small amplitude oscillatory motion around the long axis of the stem as shown. The frequency and amplitude are set in the stepper motor. The user holds the system by the handle 548 and guides the vibrating stem into the cement filled cavity in the bone.

Figure 17:
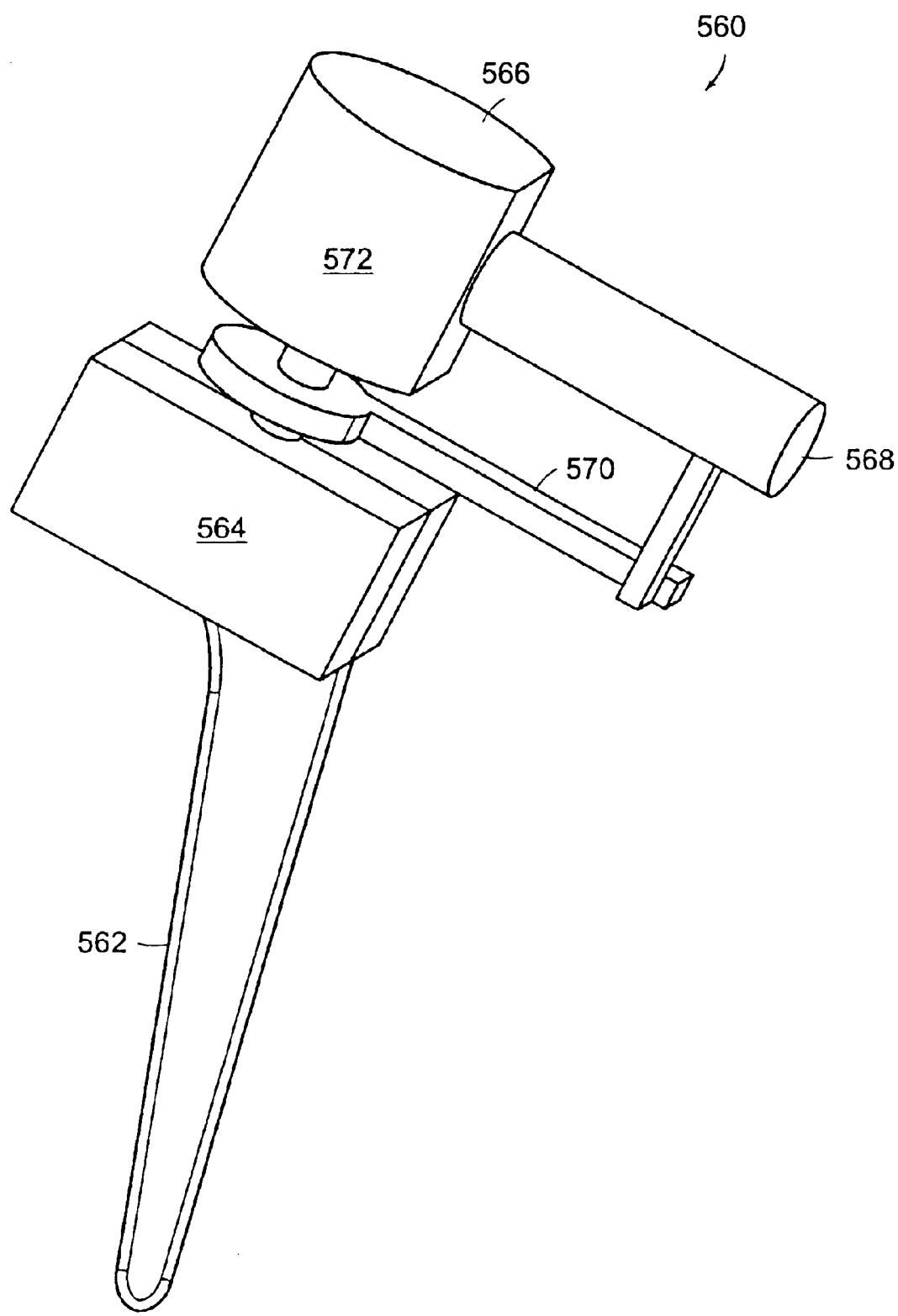
FIG. 17 schematically illustrates an apparatus used for inserting an orthopedic component using rotational shear in accordance with a preferred embodiment of the present invention.

FIG. 17 is a schematic illustration of an alternative embodiment 560 that allows rotational shear to be superimposed on the steady insertion applied by the surgeon. The stem component of the prosthetic implant 562 is held rigidly in a mounting block 564 which is in turn coupled rigidly to a lever arm 570. This lever arm is connected through a rotational coupling 572 to a handgrip 566. This coupling member 572 can be a torsional spring or a mechanical coupling or any other suitable system. The handgrip has a linear actuator mounted on an arm 568 that couples to the lever arm 570. The linear actuator could be an electromagnetic drive, or a piezoelectric system or any other suitable drive. Because the lever arm 570 has a mechanical advantage the required forces and displacement are lower than would otherwise be needed to force a rotational oscillation onto stem component of the prosthetic implant 562 whilst the surgeon inserts the implant using the handgrip. The appropriate rotational frequency and amplitude can be chosen by the operator for the specific cement being used.

Figure 18:
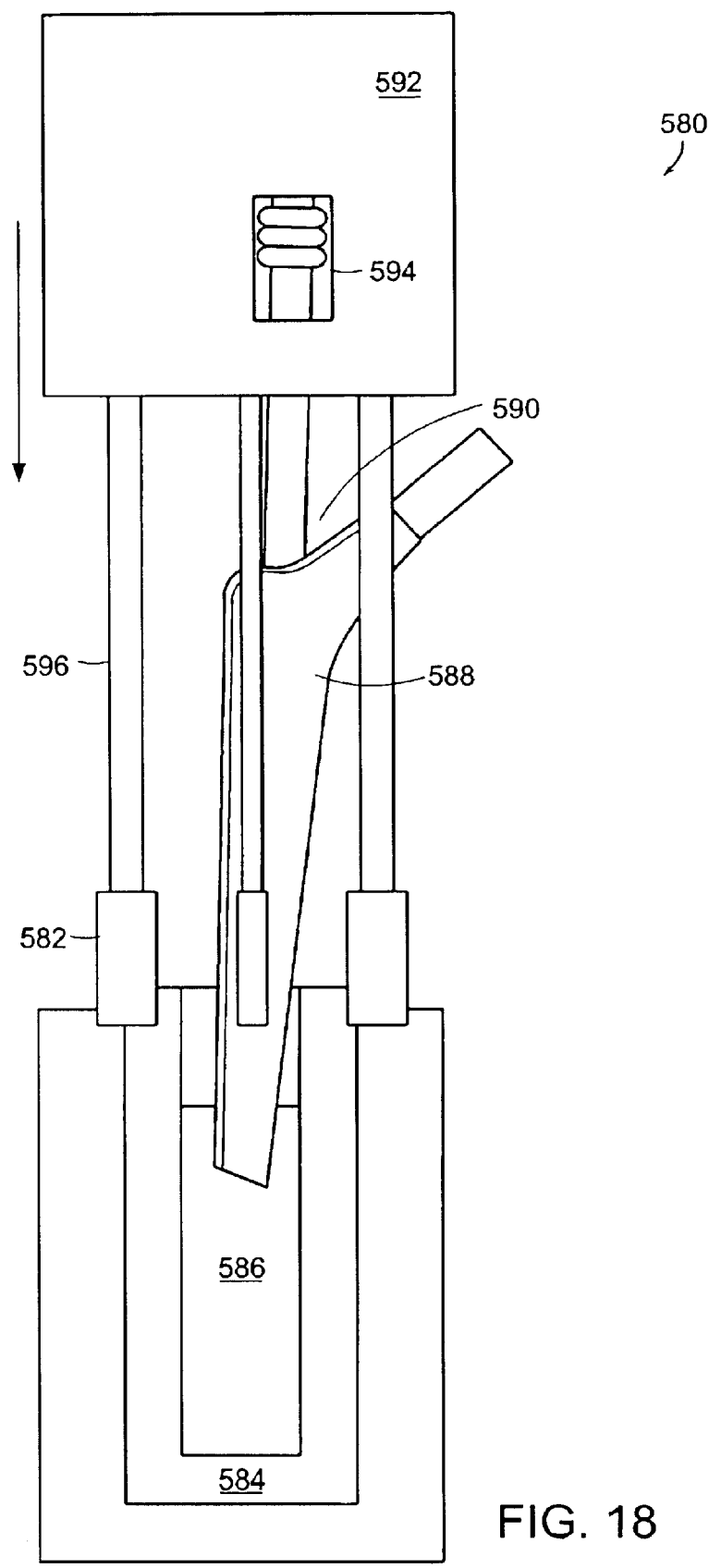
FIG. 18 schematically illustrates an automated insertion device in accordance with a preferred embodiment of the present invention.

FIG. 18 is a schematic illustration of an alternative preferred embodiment 580 that uses registration marks surgically placed on the end of the bone during surgery by the surgeon. These marks are used to rigidly locate a number of locating pins 582 on the end of the bone 584. These locating pins 582 are used to mount the insertion apparatus 582 on rigid arms 596 such that the orientation of the stem component 588 relative to the bone 584 and the cement filled cavity 586 is rigid and known and matches the desired surgical position. The only attachment between the stem component 588 and the apparatus 592 (apart from a possible lateral guidance system) is through the oscillation member 590 and an oscillation actuator 594. This oscillation actuator can be a piezoelectric oscillation actuator, an electromagnetic oscillation actuator, or an oscillation actuator based on rotational approaches as discussed hereinbefore. In addition, the apparatus 592 can move towards the bone 582 in a programmable manner thus allowing an arbitrary superimposed oscillation and steady insertion of the implant. At the end of the surgery the locating pins 582 are removed.

Figure 19:
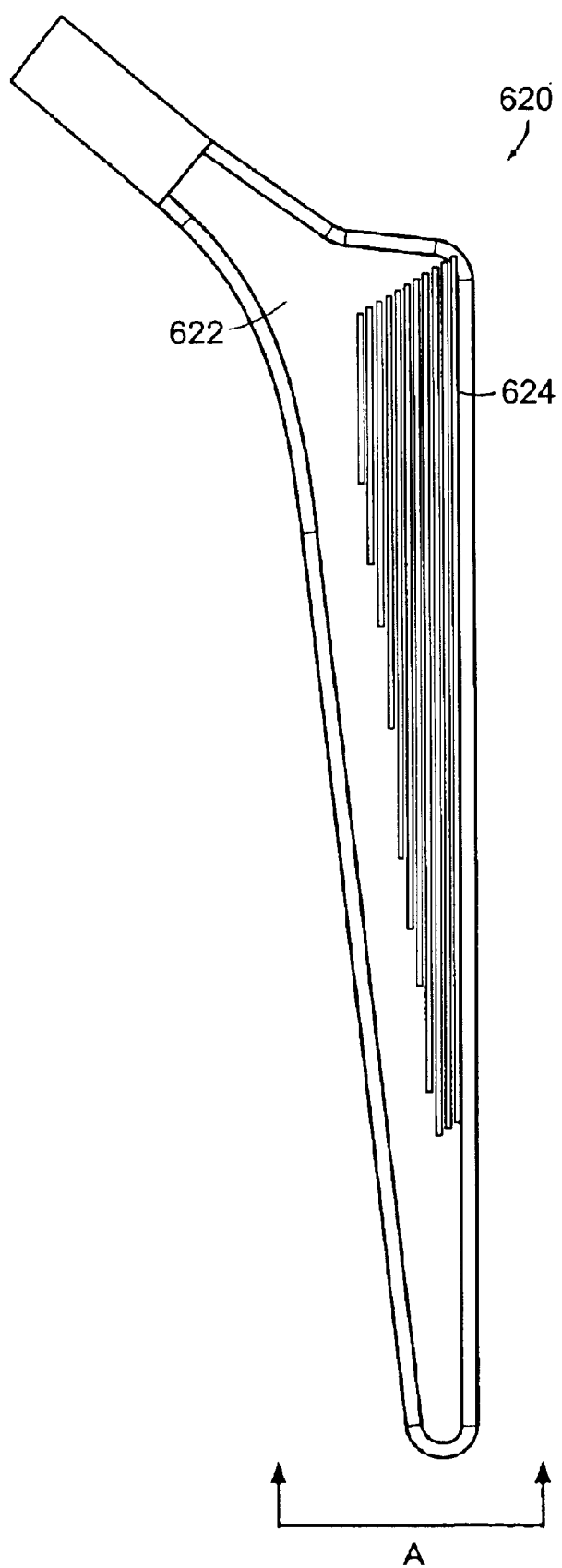
FIG. 19 is a schematic diagram of a system that includes a metallic stem having a plurality of microgrooves in accordance with a preferred embodiment of the present invention.

An additional aid to improving wetting of the bone cement on the stem as it is inserted into the cement filled cavity can be provided by longitudinal microgrooves of specific frequency and depth that are machined into the stem component. The rate of wetting has been found to increase with well-oriented grooves. This approach is used in a preferred embodiment to increase the wetting rate of the cement, and consequently reduce the extent of interfacial porosity formation. FIG. 19 is a schematic illustration of an embodiment of such a stem component 620. A plurality of microchannels 624 are formed in the body of the stem component 622 extending into the proximal end of the component 620.

Figure 20A:
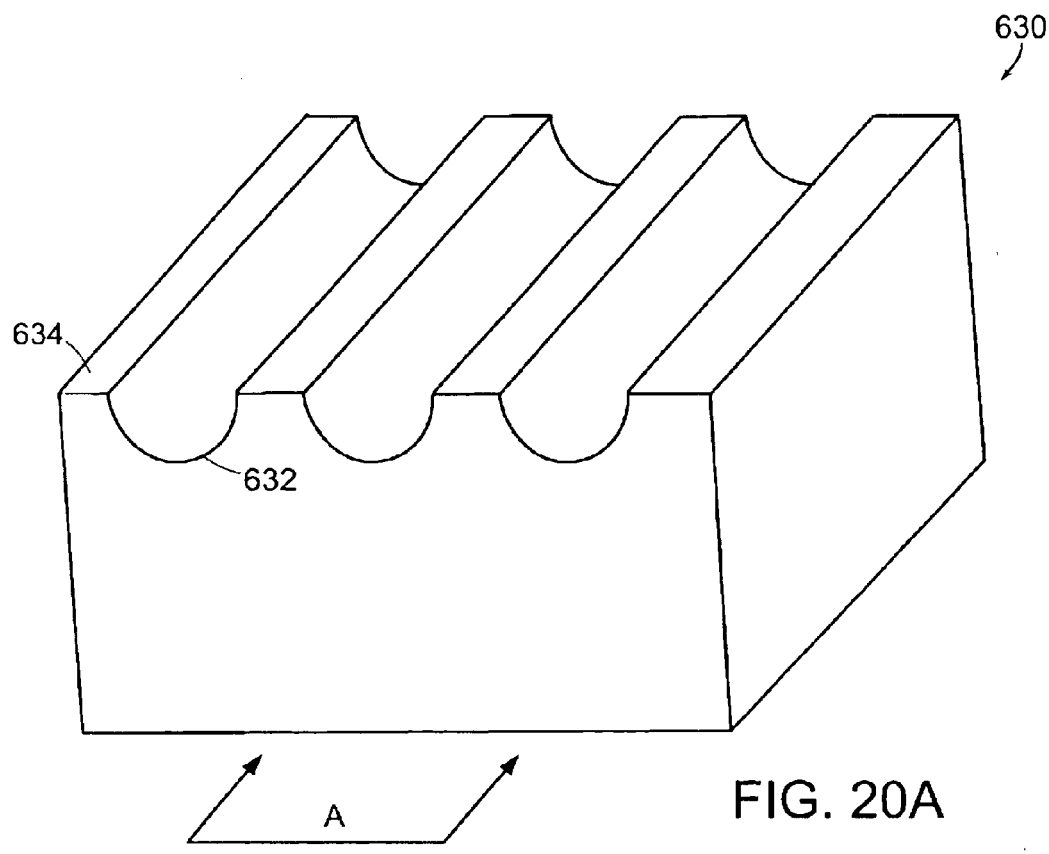
FIGS. 20A and 20B are cross-sectional views taken along line A in FIG. 19 illustrating the microgrooves having sharp edges and a smooth radius edge, respectively, in accordance with a preferred embodiment of the present invention.
Figure 20B:
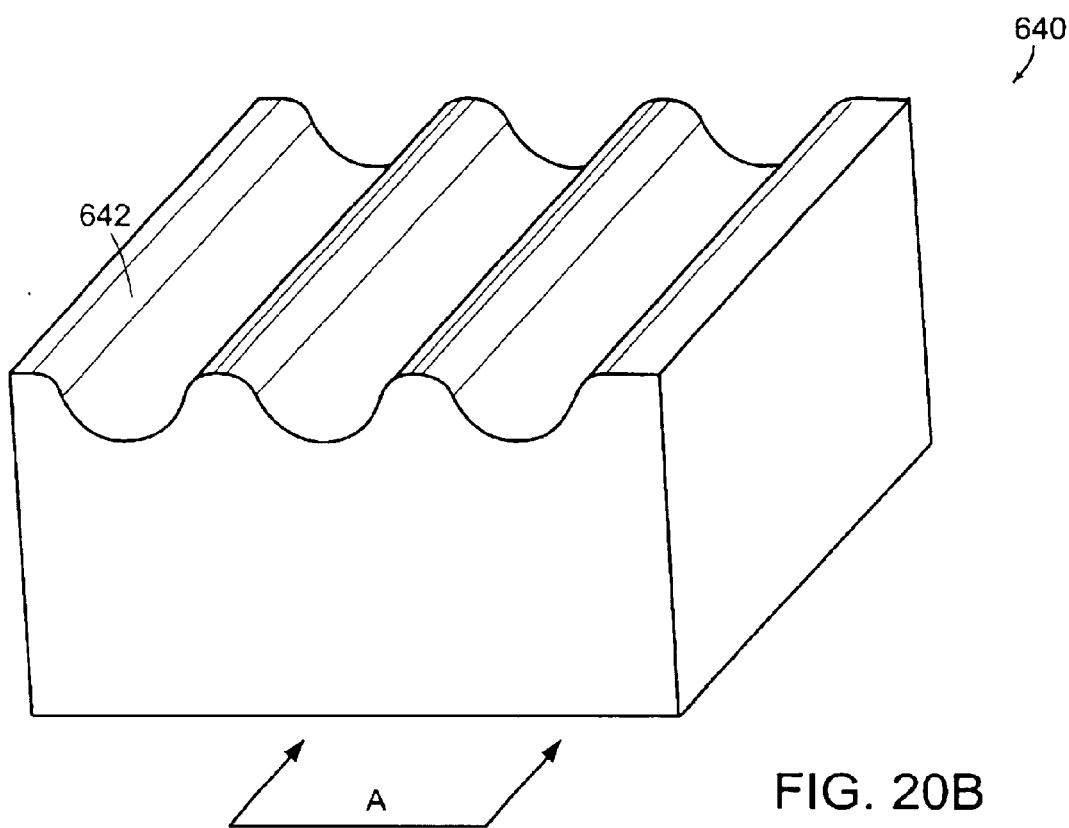

One embodiment 630 of the microchannels is shown in detail in FIG. 20A. The microchannels 632 are semicircular in cross-section with sharp edges 634. In another embodiment 640 shown in detail in FIG. 20B, the microchannels have a smooth radius edge 642. In some embodiments the radius of the microchannels is about 10 to about 1000 $\mu$m, with a center-to-center spacing of about 1.1 to about 3 times the diameter of the microchannel. In other preferred embodiments, the radius of the microchannels is about 50 to about 200 $\mu$m, with a center-to-center spacing of about 1.1 to about 3 times the diameter of the microchannel. The surface finish preferably has a surface roughness value (Ra) of about 1 to about 100 $\mu$m. The microgrooves placed around the periphery of the stem aid in wetting of the stem surface by the cement.

Figure 21:
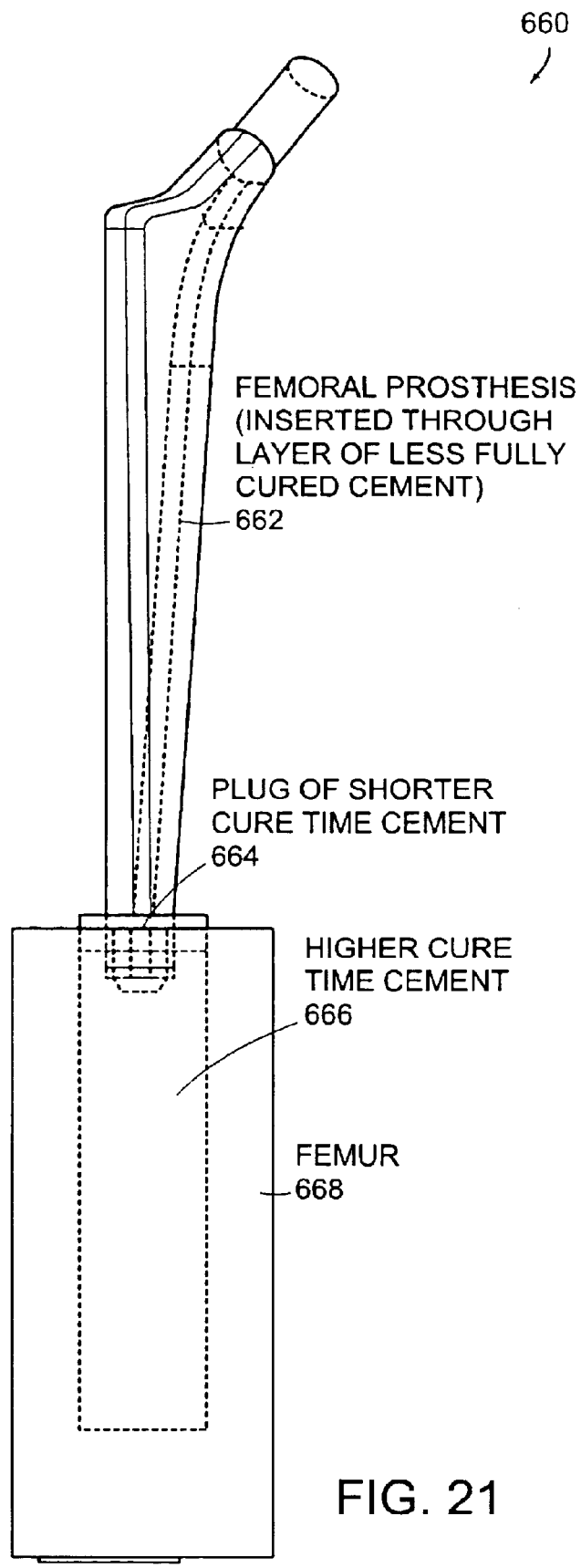
FIG. 21 schematically illustrates an alternate embodiment of a system to reduce interfacial porosity during the insertion of a prosthesis in accordance with the present invention.

Interfacial porosity also is reduced placing a thin layer of fluid with a shorter relaxation time on top of the bone cement just prior to insertion of the stem. If this fluid is substantially different from bone cement then there are issues associated with the interface between the bone cement and the fluid. However, if the material is itself bone cement at an earlier cure time, when it has a shorter relaxation time as noted above, the interface can be drastically altered without impacting or changing the material that is used to bond the prosthesis to the cement mantle. FIG. 21 is a schematic illustration of a preferred embodiment 660 in which a thin layer of partially cured cement 664 is placed on top of the more fully cured cement 666 just prior to insertion of the stem component 662 into the femur 668. In this embodiment; the contact line with air, the stem and the cement is effectively moved to the less fully cured cement, which relaxes more easily and reduces the formation of interfacial pores.

Figure 22:
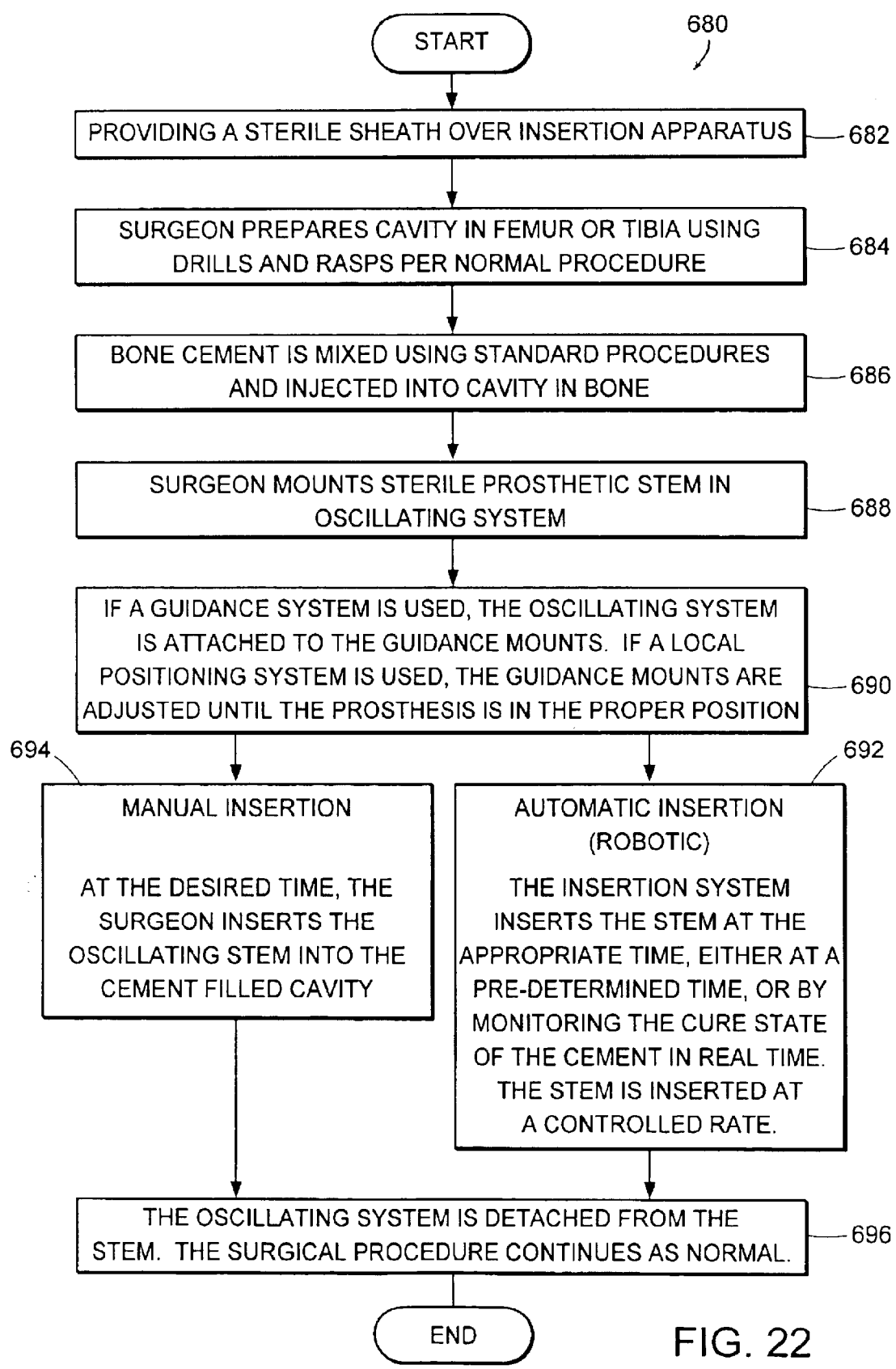
FIG. 22 is a flow chart illustrating a method for inserting a prosthesis in accordance with a preferred embodiment of the present invention.

A preferred embodiment of a method of the present invention is presented in the flow chart 680 FIG. 22. The method comprises the steps of providing a sterile sheath over the insertion device 682; preparing a cavity in the femur or tibia using drills or rasps per the normal procedure 684; mixing bone cement using standard procedures 686; injecting the mixed bone cement into the prepared cavity 688; mounting a sterile prosthetic stem component in the insertion device 688. In an embodiment in which a guidance system is used, the method further comprises the step of attaching the insertion device to the guidance mounts 690. In an embodiment in which a local positioning system is used, the method further comprises the step of adjusting the guidance mounts until the stem component of the prosthesis is in the proper position 690. In some embodiments the method further comprises the step of the surgeon inserting the oscillating stem component into the cement-filled cavity 694 at the desired time. In other embodiments the method further comprises the step of inserting the oscillating stem component into the cement-filled cavity automatically 692 at the desired time. In some embodiments the method further comprises the step of the pre-determining the appropriate time at which to insert the oscillating stem component 692. In other embodiments the method further comprises the step of the determining the appropriate time at which to insert the oscillating stem component by monitoring the cure state of the cement in real time. In preferred embodiments the method further comprises the step of monitoring the cure state of the cement in real time by measuring the force required to insert the oscillating stem component into the cement. In preferred embodiments the method further comprises the step of controlling the rate of inserting the oscillating stem component into the cement. In preferred embodiments the method further comprises the step of detaching the insertion device from the stem component 696.

Figure 23:
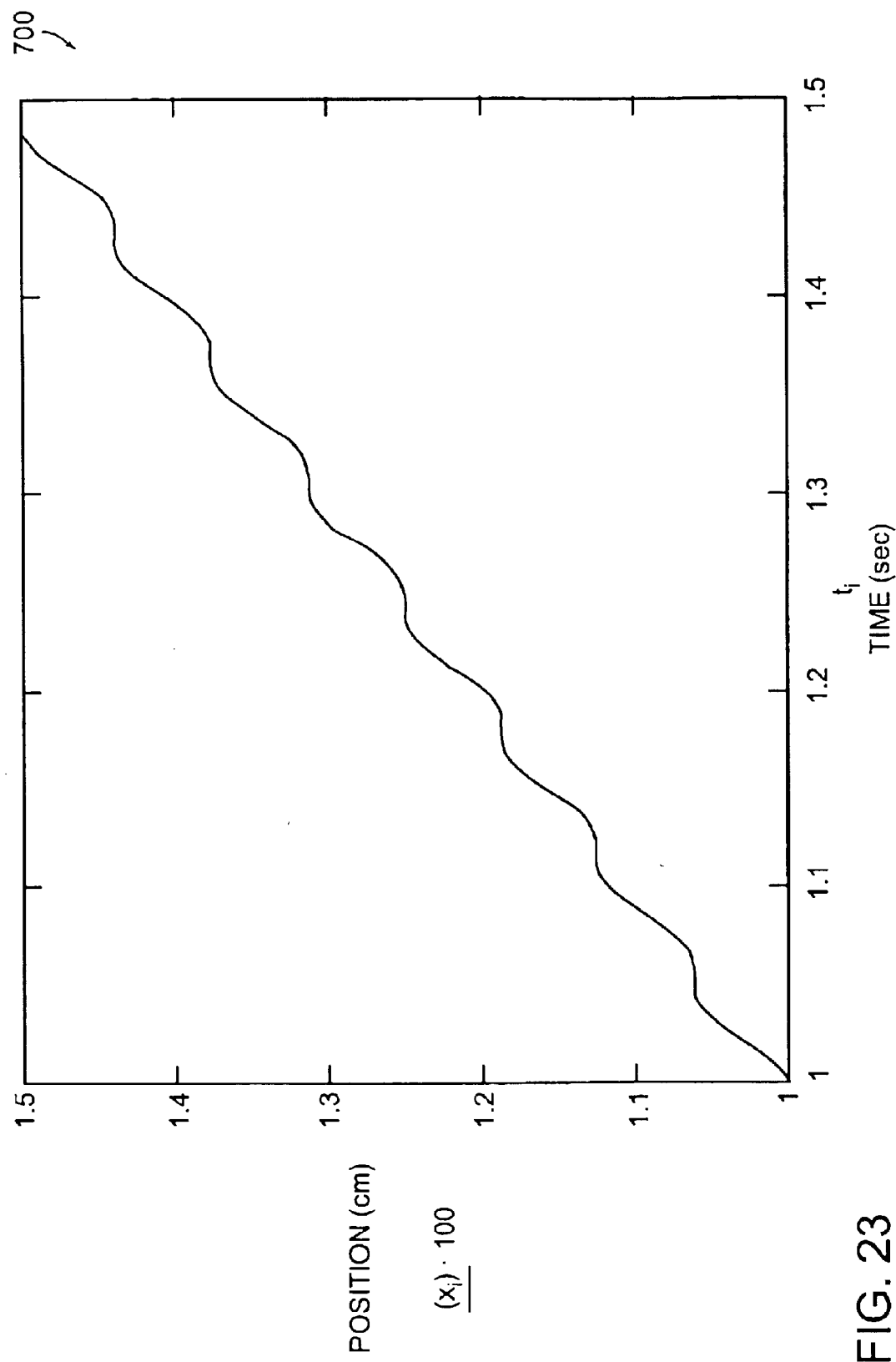
FIG. 23 graphically illustrates the relationship of the position of the inserted component to time in accordance with a preferred embodiment of the present invention.

As noted above, the change in position of the stem component with time, called herein the "insertion profile", can be varied using the system and method of the present invention by varying four parameters: oscillation frequency, oscillation amplitude, insertion velocity and stem component temperature. The particular optimum ranges of these parameters are different depending on the physical characteristics of each individual bone cement. There can be several optimum combinations of these parameters for each bone cement. An example of an insertion profile is shown graphically in FIG. 23. In this insertion profile the oscillatory displacement is superimposed on the steady insertion velocity. In other embodiments the insertion profile is characterized by one or more pauses of the insertion with continued oscillation of the stem component.

EXAMPLE 1

The results demonstrate the different interfacial porosity obtained by superimposing oscillatory motion velocity at a single fixed frequency onto a relatively steady insertion. Briefly, the experimental protocol that is followed utilizes insertion of simulated hip stem components (glass test tubes) into Howmedica Surgical Simplex P® bone cement at a cure time of 6 minutes contained in cylindrical acrylic chambers (2.5 cm diameter, 7 cm deep).

The cement is hand mixed for 30 seconds and centrifuged for 30 seconds at high speed. The top 2–3 mm of cement is scraped away to remove bubbles that migrated during the centrifugation process prior to insertion of the model stems. Both the stems were inserted at an average velocity of 1 cm/sec; in addition, one stem is also oscillated during insertion at 100 rad/sec with an estimated amplitude of 150 microns (peak-to-peak). The cured cement/stem interface are observed and photographed using a light microscope with transmission illumination.

Figure 24A:
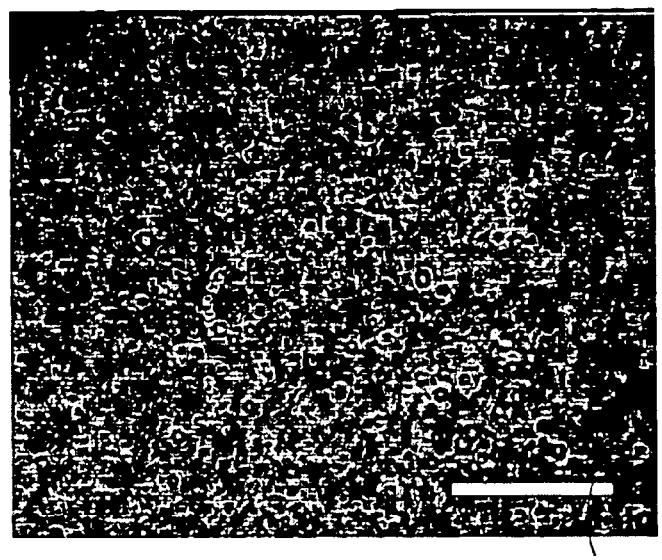
FIGS. 24A and 24B are light micrograph views of the stem/cement interface for an insertion at steady state and an oscillatory insertion, respectively, in accordance with a preferred embodiment of the present invention wherein both stems are inserted at an average velocity of 1 cm/sec.
Figure 24B:
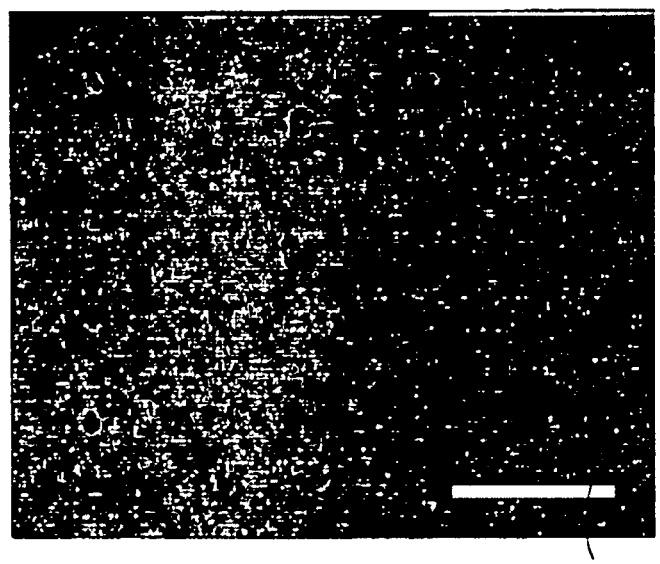

FIGS. 24A and 24B present light micrographs of the interface between the model stem and the cement. FIG. 24A illustrates the interface obtained after steady insertion at an average velocity of 1 cm/sec without oscillation. FIG. 24B illustrates the interface obtained after steady insertion at an average velocity of 1 cm/sec with an oscillation of 150 microns peak-to-peak amplitude and a frequency of 100 radians/second. Note the relative lack of small interfacial pores in FIG. 24B relative to FIG. 24A. Scale bars represent a length of 500 $\mu$m. Analysis of the images revealed 97 small-scale interfacial "pores" per square mm for insertion without oscillation compared to 1 small-scale interfacial "pores" per square mm for insertion with oscillation. The larger scale structures (100–300 microns) seen in FIG. 24A appeared smeared with indistinct borders in FIG. 24B, giving the appearance of a more uniform interfacial cement layer.

After optical examination, the cement-stem system is cooled with liquid nitrogen, and the stem is removed to allow examination of the cement interface with scanning electron microscopy. The surface of the stem is also examined with scanning electron microscopy.

EXAMPLE 2

The results demonstrate the difference interfacial porosity obtained by superposing oscillatory motion velocity at a single fixed frequency onto a slower relatively steady insertion. The experimental protocol that is in Example 1 is used, with an insertion at an average velocity of 0.25 cm/sec.

Figure 25A:
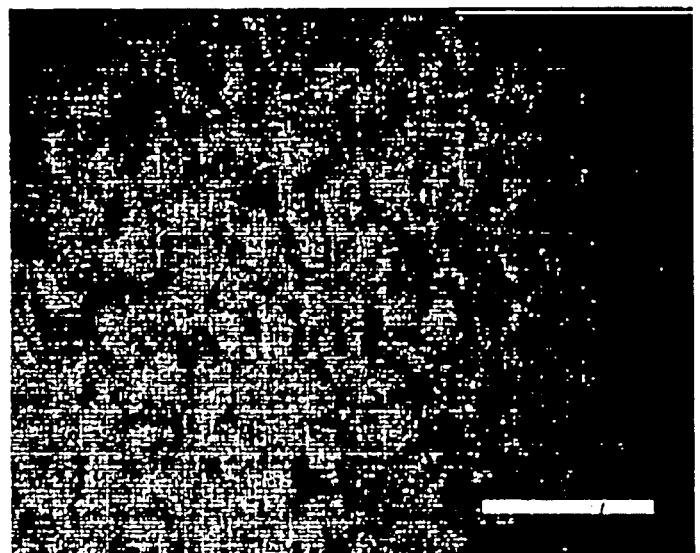
FIGS. 25A and 25B are light micrograph views of the stem/cement interface for insertion at a steady state and oscillatory, respectively, wherein the stems are inserted at an average velocity of 0.25 cm/second in accordance with a preferred embodiment of the present invention.
Figure 25B:
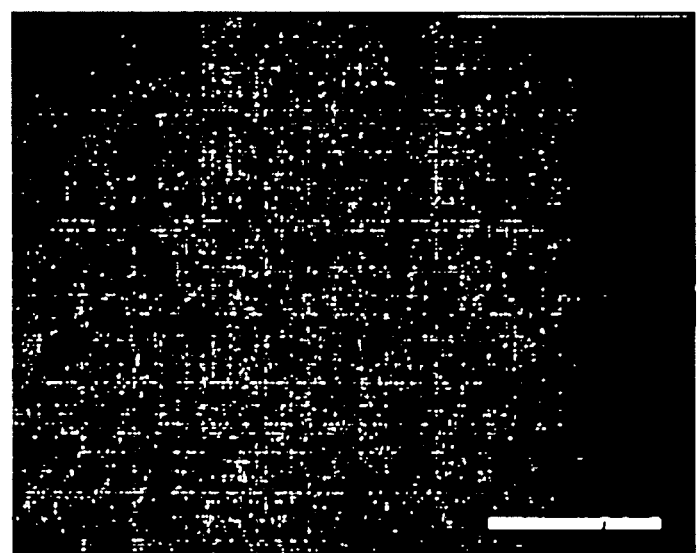

FIGS. 25A and 25B present light micrographs of the interface between the model stem and the cement. FIG. 25A illustrates the interface obtained after steady insertion at an average velocity of 0.25 cm/sec without oscillation. FIG. 25B illustrates the interface obtained after steady insertion at an average velocity of 1 cm/sec with an oscillation of 150 microns peak-to-peak amplitude and a frequency of 100 radians/second. Both images are relatively free of small scale pores. Again, larger scale structures (100–300 microns) seen in FIG. 25B appeared smeared with indistinct borders giving the general appearance of a more uniform interfacial cement layer.

After optical examination, the cement-stem system is cooled with liquid nitrogen, and the stem is removed to allow examination of the cement interface with scanning electron microscopy. The surface of the stem is also examined with scanning electron microscopy.

EXAMPLE 3

The results demonstrate the difference interfacial porosity obtained by superposing oscillatory motion velocity at a single fixed frequency relatively steady insertion with intermittent pauses. The experimental protocol that was in Example 1 was used, with an insertion at an average velocity of 0.25 cm/sec.

Figure 26A:
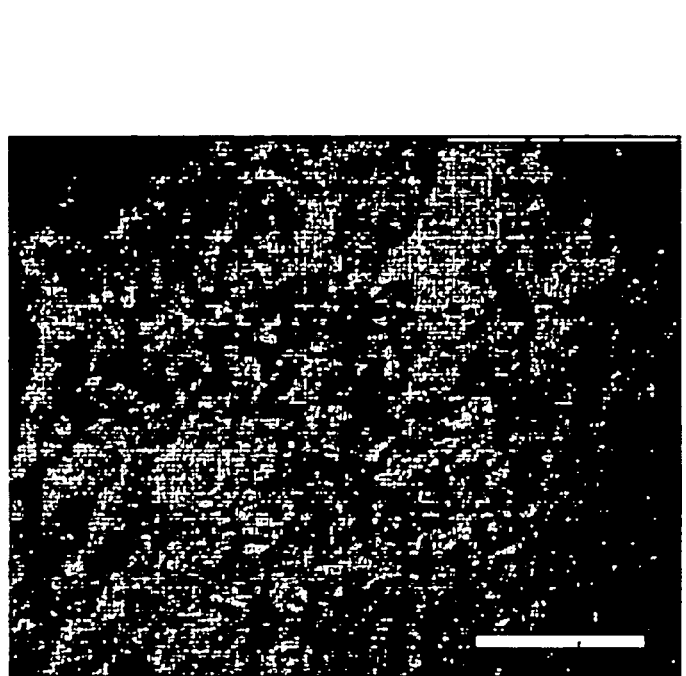
FIGS. 26A and 26B are light micrograph views of the stem/cement interface for an insertion at steady state and oscillations, respectively, wherein both stems are inserted at an average velocity of 1.0 cm/sec intermittently, in accordance with a preferred embodiment of the present invention.
Figure 26B:

FIGS. 26A and 26B present light micrographs of the interface between the model stem and the cement. FIG. 26A illustrates the interface obtained after steady insertion at an average velocity of 0.25 cm/sec without oscillation. FIG. 26B illustrates the interface obtained after steady insertion at an average velocity of 1 cm/sec with an oscillation of 150 microns peak-to-peak amplitude and a frequency of 100 radians/second. Both images are relatively free of small scale pores. Again, larger scale structures (100–300 microns) seen in FIG. 26B appeared smeared with indistinct borders giving the general appearance of a more uniform interfacial cement layer.

After optical examination, the cement-stem system is cooled with liquid nitrogen, and the stem is removed to allow examination of the cement interface with scanning electron microscopy. The surface of the stem is also examined with scanning electron microscopy.

EXAMPLE 4

Material produced in Example 1 is examined using scanning electron microscopy. Briefly, the stems are removed from the mantle at liquid nitrogen temperatures to take advantage of the differential coefficient of thermal expansions of the glass stem and the cement. The cement mantle is sectioned on a bandsaw every 1 cm and the samples were gold coated. Micrographs are taken at an acceleration voltage of 20 kV.

Figure 27A:
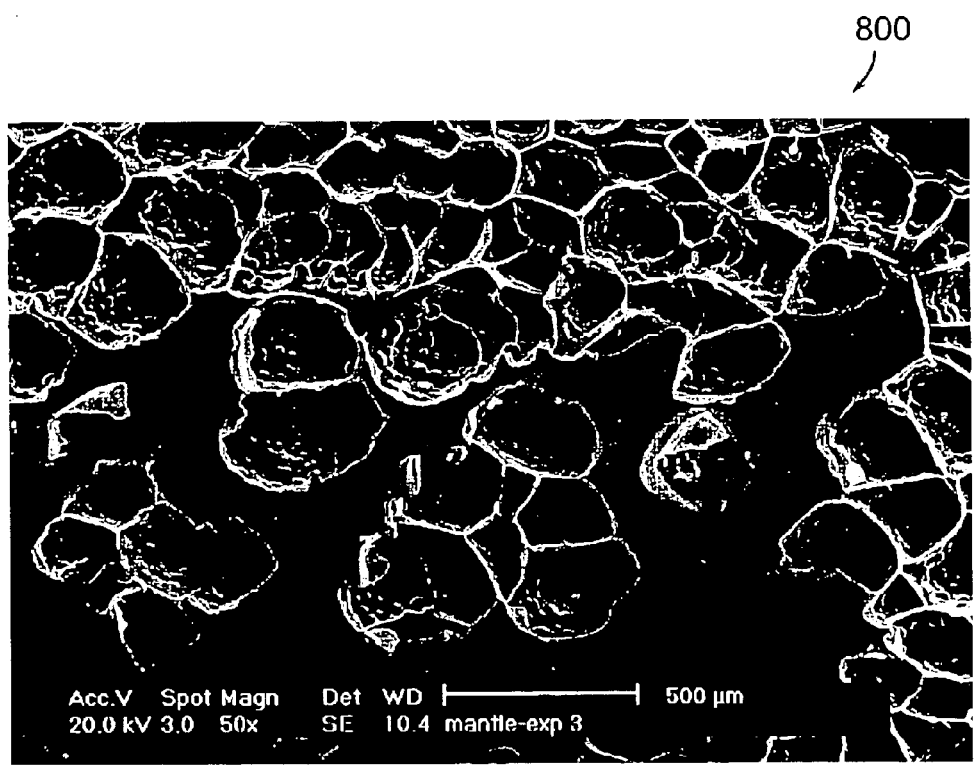
FIGS. 27A and 27B are scanning electron micrograph views of cement stem interfaces in a control system and a procedure performed in accordance with a preferred embodiment of the present invention.
Figure 27B:
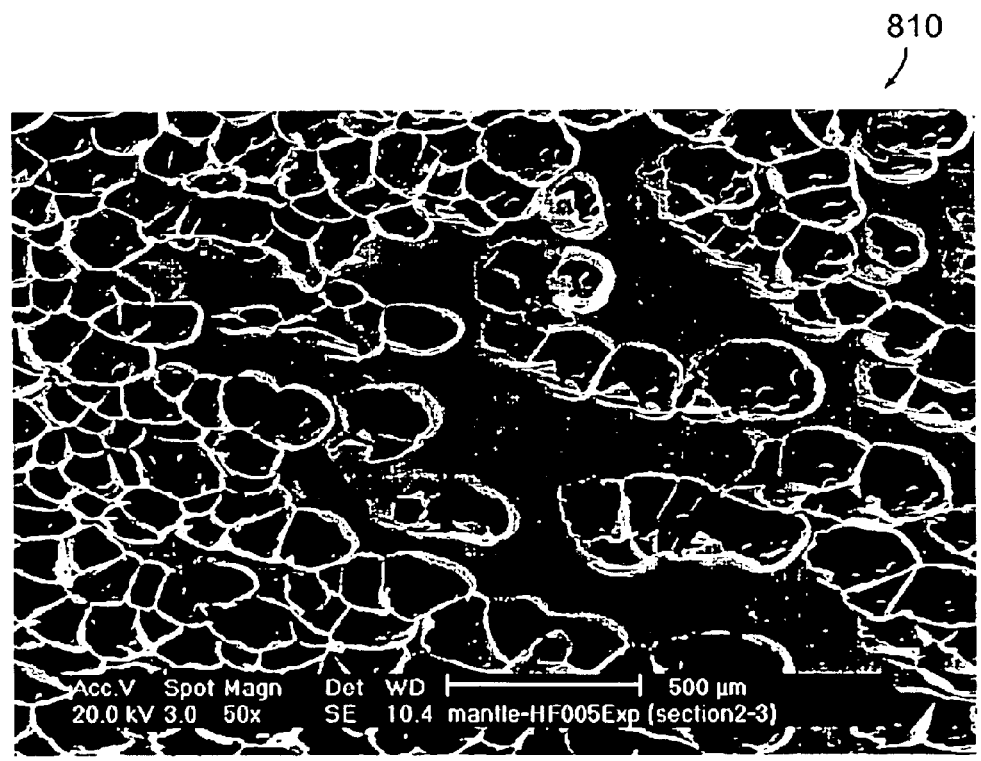
Figure 28:
FIG. 28 is a close-up scanning electron micrograph view of the cement mantle interface as shown in FIG. 27B, in accordance with a preferred embodiment of the present invention.

FIGS. 27A–27B and 28 present scanning electron micrographs of the cement surface that had been opposed to the model stem. The images reveal a difference in the average size of the pore that is formed during stem insertion. In these specimens, the average pore size of the sample without oscillation was 209 $\mu$m (FIG. 27B), while the sample with oscillation had an average pore size of 136 $\mu$m (FIG. 27B). Additionally, the bone cement layer that is in direct contact with the glass stem, when intact, appears to be comprised primarily of polymerized monomer as there is little evidence of prepolymerized beads (FIG. 28) although prepolymerized beads can be seen in the pores.

EXAMPLE 5

In order to change the contact line between the cement, stem component and air to one less conducive to pore formation, a thin layer of less cured cement is placed on top of the more cured cement that has already been placed into the simulated femur as described above and in FIG. 21. This arrangement effectively lowers the Deborah number (De) of the interfacial cement without appreciably changing the material properties of the final mantle. Eighty percent of the contents of one package (powder and monomer) of Howmedica Surgical Simplex P® was hand mixed for 30 seconds and centrifuged at high speed for 30 seconds. The cement is then poured into simulated femurs (plexiglass tubes). Three minutes following the first mixing, the remaining 20% of the cement is mixed with the remaining monomer for 30 seconds and centrifuged for 30 seconds at high speed. This second batch of cement is then poured on top of the cement already in the simulated femurs. The top layer of the first cement is removed prior to application of the second layer of cement. Two simulated prosthetic stems (glass test tubes) are inserted into the cement six minutes and 30 seconds after the initial mixing. Thus the major component of the cement has a total cure time of 6:30 while the second layer had a net cure time of 3:30. Both stems are inserted at an average velocity of 1 cm/sec. One stem is oscillated at 100 rad/sec with a peak-to-peak amplitude of 150 microns.

Figure 29A:
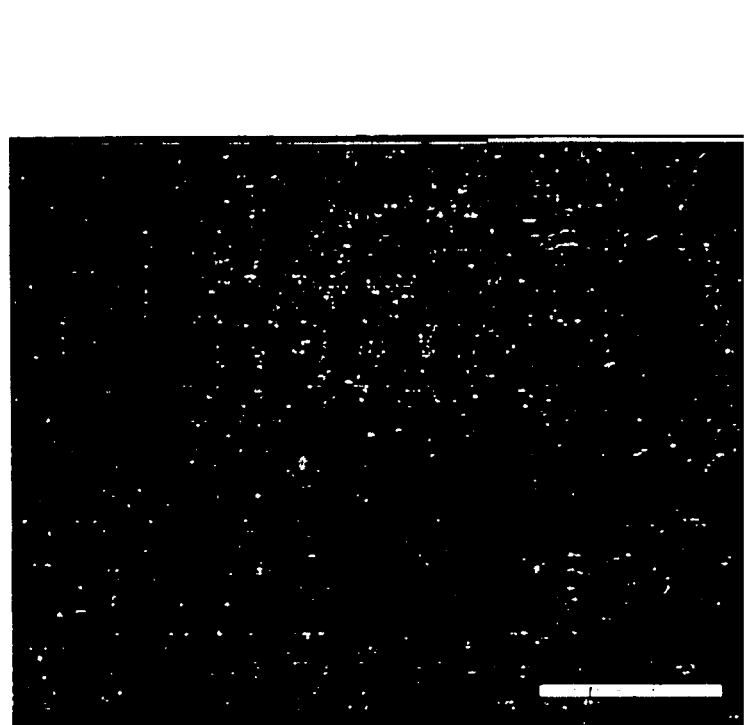
FIGS. 29A and 29B are light micrograph views comparing steady state and oscillatory shear in a procedure having a multi-layer embodiment in accordance with the present invention.
Figure 29B:
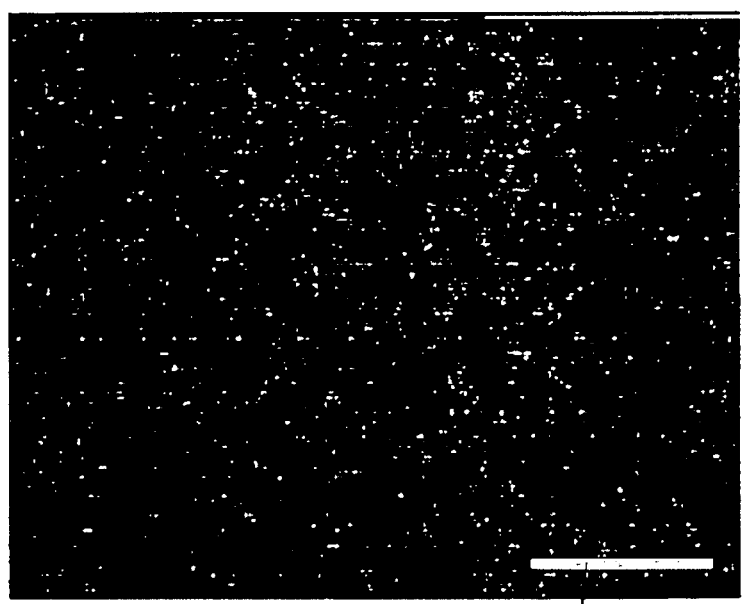

Transmission light micrographs are made as described in Example 1, above. FIGS. 29A and 29B show the results of comparison of steady shear (FIG. 29A) and steady plus oscillatory shear (FIG. 29A). Note the absence of small scale pores in both FIG. 29A and 29B, and the relatively smaller size of the interfacial structures in FIG. 29B. The scale bars represent a length of 500 microns.

The claims should not be read as limited to the described order or elements unless stated to that effect. Therefore, all embodiments that come within the scope and spirit of the following claims and equivalents thereto are claimed as the invention.

What is claimed:

1. A device for implanting a prosthesis comprising:
an actuator having a coupler that connects to a prosthesis, the prosthesis having an interface surface to be inserted into a material during implantation, the actuator comprising a housing having a transducer coupled to the prosthesis to actuate movement of the prosthesis, wherein the transducer induces vibration in the prosthesis in a range between 1 radian/second and 1000 radians/second to reduce porosity of the material at the interface surface.

2. The device of claim 1 wherein the transducer actuates vibration of the prosthesis during insertion into the material.

3. The device of claim 1 further comprising a control circuit within the housing that is electrically connected to the transducer.

4. The device of claim 1 further comprising a battery within the housing.

5. The device of claim 1 wherein the coupler comprises a thermal coupler connected to the prosthesis to control a temperature of the prosthesis.

6. The device of claim 5 further comprising a temperature sensor that measures the temperature of the prosthesis.

7. The device of claim 5 further comprising a temperature control circuit within the housing.

8. The device of claim 1 wherein the material further comprises a curable cement, the cement being inserted into a cavity in a bone of a patient.

9. The device of claim 1 further comprising a sterile sleeve extending over a housing for the actuator.

10. The device of claim 1 further comprising an actuator housing having a connector to an external power supply.

11. The device of claim 1 further comprising an actuator housing having a connector to an external control module that controls an operational parameter of the actuator.

12. The device of claim 3 wherein the control circuit comprises an oscillator, an amplifier and a processor connected to the amplifier and oscillator.

13. The device of claim 1 wherein the transducer comprises a piezoelectric driver.

14. The device of claim 1 wherein the transducer comprises a coil and a rod moving within the coil.

15. The device of claim 1 wherein the coupler comprises a pin in contact with the transducer and the prosthesis.

16. The device of claim 5 wherein the thermal coupler comprises a Peltier cell.

17. The device of claim 1 further comprising an accelerometer that measures movement of the coupler.

18. The device of claim 1 further comprising an insertion device that controls insertion of the prosthesis into the material.

19. A device for implanting a prosthesis in a patient comprising:
a housing having an actuator, and a coupler;
a prosthesis held by the housing such that the prosthesis contacts the coupler, the prosthesis having an interface surface;
a transducer coupled to the prosthesis to actuate movement of the prosthesis; and
a curable adhering material, wherein the transducer induces vibration in the prosthesis in a range between 1 radian/second and 1000 radians/second to reduce porosity of the material at the interface surface.

20. The device of claim 19 wherein the transducer actuates vibration of the prosthesis during insertion into the material.

21. The device of claim 19 further comprising a control circuit within the housing that is electrically connected to the transducer.

22. The device of claim 19 further comprising a battery within the housing and an external power supply.

23. The device of claim 19 wherein the coupler comprises a thermal coupler connected to the prosthesis to control a temperature of the prosthesis.

24. The device of claim 23 further comprising a temperature sensor that measures the temperature of the prosthesis.

25. The device of claim 23 further comprising a temperature control circuit within the housing.

26. The device of claim 19 wherein the material further comprises a curable cement, the cement being inserted into a cavity in a bone of a patient.

27. A device to reduce porosity at an interface between a bone cement and an orthopedic implant comprising:
an oscillating device that drives movement along a selected axis of the implant, the movement having a selected frequency between 1 and 1000 radians/second and selected amplitude, the oscillating device in communication with a transducer to actuate movement of the orthopedic implant.

28. The device of claim 27 wherein the oscillating device drives a plurality of frequencies and the implant has a precoating.

29. The device of claim 27 further comprising a temperature controller having an inductive heater that controls a temperature of the implant in conjunction with vibration of the implant during insertion.

30. The device of claim 27 wherein the orthopedic implant is a femoral stem.

31. The device in claim 27 wherein the orthopedic implant is a tibia tray.

32. The device in claim 27 wherein the orthopedic implant is an acetabular shell.

33. The device of claim 27 wherein the amplitude is between 1 and 500 $\mu$m.

34. The device of claim 27 wherein the insertion rate is between 0.1 and 5 cm/sec.

35. The device of claim 27 wherein the oscillating device comprises a servomotor driven oscillator.

36. The device of claim 27 wherein the oscillating device is an air-driven cam.

37. The device of claim 27 wherein the device comprises a hand-held housing.

38. The device of claim 27 further comprising a connection to a data processor and a display.

39. The device of claim 37 wherein the hand-held device comprises a port to receive a proximal end of the implant and a second port through which a pin extends along the selected axis to contact a surface of the implant.

40. The device of claim 27 further comprising a manually actuated switch on a housing to control the oscillating device.

41. The device of claim 27 wherein the oscillating device includes a control circuit, an accelerometer and a feedback circuit.

42. The device of claim 27 wherein the oscillating device comprises a rotating cam driven by a motor.

43. The device of claim 27 further comprising a mounting block in which a proximal end of the implant is mounted and an actuator to impart rotational oscillation to the distal end of the implant.

44. The device of claim 27 further comprising mounting pins that attach the device at a surgical site.

45. The device of claim 27 further comprising a programmable insertion device.

46. The device of claim 27 further comprising a disposable sterile sleeve.

47. The device of claim 39 wherein the pin is spring loaded.

48. A device for implanting a prosthesis comprising:
an actuator having a coupler that connects to a prosthesis, the actuator having an oscillator to generate oscillations at a determined frequency and amplitude, the prosthesis having an interface surface to be inserted into a material during implantation, the prosthesis being actuated at the determined frequency and amplitude to reduce porosity of the material at the interface surface and wherein the coupler comprises a thermal coupler connected to the prosthesis to control a temperature of the prosthesis.

49. The device of claim 48 wherein the actuator comprises a housing having a transducer coupled to the prosthesis to actuate movement of the prosthesis.

50. The device of claim 49 wherein the transducer actuates vibration of the prosthesis during insertion into the material.

51. The device of claim 49 further comprising a control circuit within the housing that is electrically connected to the transducer.

52. The device of claim 49 further comprising a battery within the housing.

53. The device of claim 48 further comprising a temperature sensor that measures the temperature of the prosthesis.

54. The device of claim 49 further comprising a temperature control circuit within the housing.

55. The device of claim 48 wherein the material further comprises a curable cement, the cement being inserted into a cavity in a bone of a patient.

56. The device of claim 49 wherein the transducer induces vibration in the prosthesis in a range between 1 radian/second and 1000 radians/second.

57. The device of claim 48 further comprising a sterile sleeve extending over a housing for the actuator.

58. The device of claim 48 further comprising an actuator housing having a connector to an external power supply.

59. The device of claim 48 further comprising an actuator housing having a connector to an external control module that controls an operational parameter of the actuator.

60. The device of claim 51 wherein the control circuit comprises an oscillator, an amplifier and a processor connected to the amplifier and oscillator.

61. The device of claim 49 wherein the transducer comprises a piezoelectric driver.

62. The device of claim 49 wherein the transducer comprises a coil and a rod moving within the coil.

63. The device of claim 49 wherein the coupler comprises a pin in contact with the transducer and the prosthesis.

64. The device of claim 48 wherein the thermal coupler comprises a Peltier cell.

65. The device of claim 49 further comprising an accelerometer that measures movement of the coupler.

66. The device of claim 48 further comprising an insertion device that controls insertion of the prosthesis into the material.

67. A device to reduce porosity at an interface between a bone cement and an orthopedic implant comprising:
an oscillating device that drives movement along a selected axis of the implant, the movement having a selected frequency and amplitude, the oscillating device in communication with a transducer to actuate movement of the orthopedic implant, wherein the insertion rate of the orthopedic implant is between 0.1 and 10 cm/sec.

68. The device of claim 67 wherein the oscillating device drives a plurality of frequencies and the implant has a precoating.

69. The device of claim 67 further comprising a temperature controller having an inductive heater that controls a temperature of the implant in conjunction with vibration of the implant during insertion.

70. The device of claim 67 wherein the orthopedic implant is a femoral stem.

71. The device in claim 67 wherein the orthopedic implant is a tibia tray.

72. The device in claim 67 wherein the orthopedic implant is an acetabular shell.

73. The device of claim 67 wherein the frequency is between 1 and 1000 rad/sec.

74. The device of claim 67 wherein the amplitude is between 1 and 500 $\mu$m.

75. The device of claim 67 wherein the oscillating device comprises a servomotor driven oscillator.

76. The device of claim 67 wherein the oscillating device is an air-driven cam.

77. The device of claim 67 wherein the device comprises a hand-held housing.

78. The device of claim 67 further comprising a connection to a data processor and a display.

79. The device of claim 77 wherein the hand-held device comprises a port to receive a proximal end of the implant and a second port through which a pin extends along the selected axis to contact a surface of the implant.

80. The device of claim 67 further comprising a manually actuated switch on a housing to control the oscillating device.

81. The device of claim 67 wherein the oscillating device includes a control circuit, an accelerometer and a feedback circuit.

82. The device of claim 67 wherein the oscillating device comprises a rotating cam driven by a motor.

* * * * *